US008492539B2

(12) United States Patent
Chun et al.

(10) Patent No.: US 8,492,539 B2
(45) Date of Patent: *Jul. 23, 2013

(54) PREPARATION OF 2'-FLUORO-2'-ALKYL-SUBSTITUTED OR OTHER OPTIONALLY SUBSTITUTED RIBOFURANOSYL PYRIMIDINES AND PURINES AND THEIR DERIVATIVES

(75) Inventors: Byoung-Kwon Chun, Robbinsville, NJ (US); Peiyuan Wang, Glen Rock, NJ (US); Jinfa Du, New Hope, PA (US); Suguna Rachakonda, Robbinsville, NJ (US)

(73) Assignee: Gilead Pharmasset LLC, Foster City, CA (US)

(*) Notice: Subject to any disclaimer, the term of this patent is extended or adjusted under 35 U.S.C. 154(b) by 1547 days.

This patent is subject to a terminal disclaimer.

(21) Appl. No.: 11/225,425

(22) Filed: Sep. 13, 2005

(65) Prior Publication Data
US 2006/0122146 A1 Jun. 8, 2006

Related U.S. Application Data

(60) Provisional application No. 60/609,783, filed on Sep. 14, 2004, provisional application No. 60/610,035, filed on Sep. 15, 2004, provisional application No. 60/666,230, filed on Mar. 29, 2005.

(51) Int. Cl.
*C07H 1/00* (2006.01)
*C07H 3/00* (2006.01)
*C07H 19/00* (2006.01)
*C07H 21/00* (2006.01)
*C07D 307/00* (2006.01)

(52) U.S. Cl.
USPC .......... 536/124; 536/1.11; 536/22.1; 549/313

(58) Field of Classification Search
None
See application file for complete search history.

(56) References Cited

U.S. PATENT DOCUMENTS

| | | | |
|---|---|---|---|
| 3,798,209 A | 3/1974 | Witkowski et al. | |
| RE29,835 E | 11/1978 | Witkowski | |
| 4,526,988 A | 7/1985 | Hertel | |
| 4,808,614 A | 2/1989 | Hertel | |
| 4,814,477 A | 3/1989 | Wijnberg et al. | |
| 4,957,924 A | 9/1990 | Beauchamp | |
| 5,026,687 A | 6/1991 | Yarchoan et al. | |
| 5,118,820 A | 6/1992 | Hertel | |
| 5,149,794 A | 9/1992 | Yatvin et al. | |
| 5,157,027 A | 10/1992 | Biller et al. | |
| 5,194,654 A | 3/1993 | Hostetler et al. | |
| 5,223,263 A | 6/1993 | Hostetler et al. | |
| 5,256,641 A | 10/1993 | Yatvin et al. | |
| 5,256,798 A | 10/1993 | Chou et al. | |
| 5,372,808 A | 12/1994 | Blatt et al. | |
| 5,405,598 A | 4/1995 | Schinazi et al. | |
| 5,411,947 A | 5/1995 | Hostetler et al. | |
| 5,420,266 A | 5/1995 | Britton et al. | |
| 5,426,183 A | 6/1995 | Kjell | |
| 5,446,139 A | 8/1995 | Seela et al. | |
| 5,453,499 A | 9/1995 | Chou et al. | |
| 5,462,724 A | 10/1995 | Schinazi et al. | |
| 5,463,092 A | 10/1995 | Hostetler et al. | |
| 5,496,546 A | 3/1996 | Wang et al. | |
| 5,538,865 A | 7/1996 | Reyes et al. | |
| 5,543,389 A | 8/1996 | Yatvin et al. | |
| 5,543,390 A | 8/1996 | Yatvin et al. | |
| 5,543,391 A | 8/1996 | Yatvin et al. | |
| 5,554,728 A | 9/1996 | Basava et al. | |
| 5,610,054 A | 3/1997 | Draper | |
| 5,631,239 A | 5/1997 | Lin et al. | |
| 5,633,358 A | 5/1997 | Gruetzke et al. | |
| 5,633,388 A | 5/1997 | Diana et al. | |
| 5,676,942 A | 10/1997 | Testa et al. | |
| 5,703,058 A | 12/1997 | Schinazi et al. | |
| 5,711,944 A | 1/1998 | Gilbert et al. | |
| 5,725,859 A | 3/1998 | Omer | |
| 5,738,845 A | 4/1998 | Imakawa | |
| 5,738,846 A | 4/1998 | Greenwald et al. | |
| 5,747,646 A | 5/1998 | Hakimi et al. | |
| 5,767,097 A | 6/1998 | Tam | |
| 5,792,834 A | 8/1998 | Hakimi et al. | |
| 5,830,455 A | 11/1998 | Valtuena et al. | |
| 5,830,905 A | 11/1998 | Diana et al. | |
| 5,834,594 A | 11/1998 | Hakimi et al. | |
| 5,837,257 A | 11/1998 | Tsai et al. | |

(Continued)

FOREIGN PATENT DOCUMENTS

CA 2527657 A1 1/2005
DE 19914474 A1 3/1998

(Continued)

OTHER PUBLICATIONS

Goekjian et al., Journal of Organic Chemistry, 1999, 64(12), 4238-4246.*
Novak et al., Collection of Czechoslovak Chemical Communications, vol. 39, pp. 869-882, 1974.*
Walton et al., Journal of the American Chemical Society (1966), 88(19), 4524-5.*
Sun Xiao-Ling and Wu Yu-Lin, "Study on the Chirality of Sulfur in Ethyl (2S,3R,4R)-4,5- O-Isopropylidene-2-3-sulfinyl-2,3,4,5-tetrahydroxy-pentanoate", Acta Chimica Sinica, 1997, vol. 55, pp. 600-604.

(Continued)

*Primary Examiner* — Traviss C McIntosh, III
(74) *Attorney, Agent, or Firm* — Fitzpatrick, Cella, Harper & Scinto

(57) ABSTRACT

The present invention provides (i) processes for preparing a 2'-deoxy-2'-fluoro-2'-methyl-D-ribonolactone derivatives, (ii) conversion of intermediate lactones to nucleosides with potent anti-HCV activity, and their analogues, and (iii) methods to prepare the anti-HCV nucleosides containing the 2'-deoxy-2'-fluoro-2'-C-methyl-β-D-ribofuranosyl nucleosides from a preformed, preferably naturally-occurring, nucleoside.

7 Claims, No Drawings

U.S. PATENT DOCUMENTS

| | | | |
|---|---|---|---|
| 5,846,964 A | 12/1998 | Ozeki | |
| 5,849,696 A | 12/1998 | Chretien et al. | |
| 5,869,253 A | 2/1999 | Draper | |
| 5,891,874 A | 4/1999 | Colacino et al. | |
| 5,905,070 A | 5/1999 | Schinazi et al. | |
| 5,908,621 A | 6/1999 | Glue et al. | |
| 5,922,757 A | 7/1999 | Chojkier | |
| 5,928,636 A | 7/1999 | Alber et al. | |
| 5,942,223 A | 8/1999 | Bazer et al. | |
| 5,977,325 A | 11/1999 | McCarthy et al. | |
| 5,980,884 A | 11/1999 | Blatt et al. | |
| 5,990,276 A | 11/1999 | Zhang et al. | |
| 6,004,933 A | 12/1999 | Spruce et al. | |
| 6,034,134 A | 3/2000 | Gold et al. | |
| 6,043,077 A | 3/2000 | Barber et al. | |
| 6,056,961 A | 5/2000 | Lavie et al. | |
| 6,090,932 A | 7/2000 | McGee et al. | |
| 6,130,326 A | 10/2000 | Ramasamy et al. | |
| 6,156,501 A | 12/2000 | McGall et al. | |
| 6,232,300 B1 | 5/2001 | Schinazi et al. | |
| 6,239,159 B1 | 5/2001 | Brown et al. | |
| 6,348,587 B1 | 2/2002 | Schinazi et al. | |
| 6,372,883 B1 | 4/2002 | Attwood et al. | |
| 6,391,859 B1 | 5/2002 | Schinazi et al. | |
| 6,410,531 B1 | 6/2002 | Llinas-Brunet et al. | |
| 6,420,380 B2 | 7/2002 | Llinas-Brunet et al. | |
| 6,455,513 B1 | 9/2002 | McGuigan et al. | |
| 6,455,690 B1 | 9/2002 | Tam et al. | |
| 6,479,463 B1 | 11/2002 | Wang et al. | |
| 6,495,677 B1 | 12/2002 | Ramasamy et al. | |
| 6,509,320 B1 | 1/2003 | Wang et al. | |
| 6,534,523 B1 | 3/2003 | Llinas-Brunet et al. | |
| 6,552,183 B1 | 4/2003 | Ramasamy et al. | |
| 6,555,677 B2 | 4/2003 | Petrillo et al. | |
| 6,573,248 B2 | 6/2003 | Ramasamy et al. | |
| 6,642,206 B2 | 11/2003 | Ramasamy et al. | |
| 6,660,721 B2 | 12/2003 | Devos et al. | |
| 6,677,314 B2 | 1/2004 | Klecker et al. | |
| 6,677,315 B2 | 1/2004 | Klecker et al. | |
| 6,680,303 B2 | 1/2004 | Schinazi et al. | |
| 6,682,715 B2 | 1/2004 | Klecker et al. | |
| 6,683,045 B2 | 1/2004 | Klecker et al. | |
| 6,703,374 B1 | 3/2004 | Klecker et al. | |
| 6,753,309 B2 | 6/2004 | Klecker et al. | |
| 6,777,395 B2 | 8/2004 | Bhat et al. | |
| 6,787,305 B1 | 9/2004 | Li et al. | |
| 6,787,526 B1 | 9/2004 | Bryant et al. | |
| 6,815,542 B2 | 11/2004 | Hong et al. | |
| 6,897,201 B2 | 5/2005 | Boyer et al. | |
| 6,908,924 B2 | 6/2005 | Watanabe et al. | |
| 6,914,054 B2 | 7/2005 | Sommadossi et al. | |
| 6,962,991 B2 | 11/2005 | Dempcy et al. | |
| 7,018,985 B1 | 3/2006 | Boyer et al. | |
| 7,018,989 B2 | 3/2006 | McGuigan et al. | |
| 7,081,449 B2 | 7/2006 | Pietrzkowski et al. | |
| 2002/0058635 A1 | 5/2002 | Averett | |
| 2002/0198173 A1 | 12/2002 | Schinazi et al. | |
| 2003/0050229 A1 | 3/2003 | Sommadossi et al. | |
| 2003/0060400 A1 | 3/2003 | LaColla et al. | |
| 2003/0120071 A1 | 6/2003 | McGuigan et al. | |
| 2003/0144502 A1 | 7/2003 | Pietrzkowski et al. | |
| 2003/0153744 A1 | 8/2003 | Mekouar et al. | |
| 2004/0006007 A1 | 1/2004 | Gosselin et al. | |
| 2004/0014108 A1 | 1/2004 | Elarup et al. | |
| 2004/0023240 A1 | 2/2004 | Marliere et al. | |
| 2004/0023901 A1 | 2/2004 | Cook et al. | |
| 2004/0059104 A1 | 3/2004 | Cook et al. | |
| 2004/0063622 A1 | 4/2004 | Sommadossi et al. | |
| 2004/0067901 A1 | 4/2004 | Bhat et al. | |
| 2004/0072788 A1 | 4/2004 | Bhat et al. | |
| 2004/0097461 A1 | 5/2004 | Sommadossi et al. | |
| 2004/0097462 A1 | 5/2004 | Sommadossi et al. | |
| 2004/0101535 A1 | 5/2004 | Sommadossi et al. | |
| 2004/0102414 A1 | 5/2004 | Sommadossi et al. | |
| 2004/0110717 A1 | 6/2004 | Carroll et al. | |
| 2004/0167140 A1 | 8/2004 | Schinazi et al. | |
| 2004/0191824 A1 | 9/2004 | Dempcy et al. | |
| 2004/0214844 A1 | 10/2004 | Otto et al. | |
| 2004/0229839 A1 | 11/2004 | Babu et al. | |
| 2004/0248892 A1 | 12/2004 | Wang | |
| 2004/0254141 A1 | 12/2004 | Schinazi et al. | |
| 2004/0259934 A1 | 12/2004 | Olsen et al. | |
| 2004/0265969 A1 | 12/2004 | Li et al. | |
| 2004/0266996 A1 | 12/2004 | Rabi | |
| 2005/0004357 A1 | 1/2005 | Moussa et al. | |
| 2005/0009737 A1 | 1/2005 | Clark | |
| 2005/0020825 A1 | 1/2005 | Storer et al. | |
| 2005/0026853 A1 | 2/2005 | Mekouar et al. | |
| 2005/0031588 A1 | 2/2005 | Sommadassi et al. | |
| 2005/0075309 A1 | 4/2005 | Storer et al. | |
| 2005/0080034 A1 | 4/2005 | Standring et al. | |
| 2005/0090660 A1 | 4/2005 | Watanabe et al. | |
| 2005/0124532 A1 | 6/2005 | Sommadossi et al. | |
| 2005/0130931 A1 | 6/2005 | Boyer et al. | |
| 2005/0137161 A1 | 6/2005 | Sommadossi et al. | |
| 2005/0148534 A1 | 7/2005 | Castellino et al. | |
| 2005/0164960 A1 | 7/2005 | Olsen et al. | |
| 2005/0215513 A1 | 9/2005 | Boojamra et al. | |
| 2005/0227947 A1 | 10/2005 | Chan et al. | |
| 2005/0261237 A1 | 11/2005 | Boojamra et al. | |
| 2006/0003951 A1 | 1/2006 | Mekouar et al. | |
| 2006/0014943 A1 | 1/2006 | Dempcy et al. | |
| 2006/0035866 A1 | 2/2006 | Cannizzaro et al. | |
| 2006/0040944 A1 | 2/2006 | Gosselin et al. | |
| 2006/0079478 A1 | 4/2006 | Boojamra et al. | |
| 2006/0110727 A9 | 5/2006 | McGall et al. | |
| 2006/0122146 A1 | 6/2006 | Chun et al. | |
| 2006/0122154 A1 | 6/2006 | Olsen et al. | |
| 2006/0142238 A1 | 6/2006 | McGuigan | |
| 2006/0144502 A1 | 7/2006 | Weder | |

FOREIGN PATENT DOCUMENTS

| | | |
|---|---|---|
| EP | 180276 A1 | 10/1984 |
| EP | 0285884 A2 | 10/1988 |
| EP | 350287 B1 | 7/1989 |
| EP | 0352248 A1 | 1/1990 |
| EP | 0457326 A1 | 11/1991 |
| EP | 0805158 A2 | 11/1997 |
| EP | 805158 | 4/1998 |
| GB | 1209654 A | 10/1970 |
| JP | 59175498 | 10/1984 |
| JP | 2002504558 A | 2/2002 |
| JP | 2004520367 A | 7/2004 |
| NO | 20050465 A | 1/2005 |
| WO | WO8902733 A1 | 4/1989 |
| WO | WO9000555 A1 | 1/1990 |
| WO | WO9116920 A1 | 11/1991 |
| WO | WO9118914 A1 | 12/1991 |
| WO | WO9119721 A1 | 12/1991 |
| WO | WO9300910 A1 | 1/1993 |
| WO | WO9426273 A1 | 11/1994 |
| WO | WO9513090 A1 | 5/1995 |
| WO | WO 95/24185 | 9/1995 |
| WO | 96/13512 A2 | 5/1996 |
| WO | WO9615132 A1 | 5/1996 |
| WO | 96/29336 A1 | 9/1996 |
| WO | WO 96/32403 | 10/1996 |
| WO | WO9736554 A1 | 10/1997 |
| WO | 97/41127 A1 | 11/1997 |
| WO | WO 98/16184 | 4/1998 |
| WO | WO9817679 A1 | 4/1998 |
| WO | WO9822496 A2 | 5/1998 |
| WO | WO9822496 A3 | 5/1998 |
| WO | WO9907734 A2 | 2/1999 |
| WO | WO9907734 A3 | 2/1999 |
| WO | WO9915194 A1 | 4/1999 |
| WO | WO9932139 A1 | 7/1999 |
| WO | WO9932140 A1 | 7/1999 |
| WO | 9943691 | 9/1999 |
| WO | WO9943691 A1 | 9/1999 |
| WO | WO9959621 A1 | 11/1999 |
| WO | WO9964016 A1 | 12/1999 |
| WO | WO0009531 A2 | 2/2000 |
| WO | WO0024355 A1 | 5/2000 |
| WO | WO0037110 A2 | 6/2000 |
| WO | WO0037110 A3 | 6/2000 |
| WO | WO0132153 A2 | 5/2001 |

| | | |
|---|---|---|
| WO | WO01060315 A3 | 8/2001 |
| WO | WO01060315 R4 | 8/2001 |
| WO | WO0179246 A2 | 10/2001 |
| WO | WO01079246 A3 | 10/2001 |
| WO | WO01079246 R4 | 10/2001 |
| WO | WO0181359 A1 | 11/2001 |
| WO | WO0190121 A3 | 11/2001 |
| WO | WO0190121 R4 | 11/2001 |
| WO | WO0191737 A2 | 12/2001 |
| WO | WO0192282 A3 | 12/2001 |
| WO | WO0192282 R4 | 12/2001 |
| WO | WO0196353 A2 | 12/2001 |
| WO | WO0196353 A3 | 12/2001 |
| WO | WO0196353 R4 | 12/2001 |
| WO | 02/08256 A2 | 1/2002 |
| WO | WO0208187 A1 | 1/2002 |
| WO | WO0208187 R6 | 1/2002 |
| WO | WO0208198 A2 | 1/2002 |
| WO | WO0208198 A3 | 1/2002 |
| WO | WO0208198 R4 | 1/2002 |
| WO | WO0208251 A2 | 1/2002 |
| WO | WO0208251 A3 | 1/2002 |
| WO | WO0208251 R4 | 1/2002 |
| WO | WO0208256 A2 | 1/2002 |
| WO | 02/18404 A2 | 3/2002 |
| WO | WO0232414 A3 | 4/2002 |
| WO | WO0232414 R4 | 4/2002 |
| WO | WO0232920 A2 | 4/2002 |
| WO | WO0232920 A3 | 4/2002 |
| WO | WO0232920 R4 | 4/2002 |
| WO | WO 02/42172 | 6/2002 |
| WO | WO 02/49165 | 6/2002 |
| WO | WO0248116 A2 | 6/2002 |
| WO | WO0248157 A2 | 6/2002 |
| WO | WO0248157 R4 | 6/2002 |
| WO | WO0248165 A2 | 6/2002 |
| WO | WO0248165 A3 | 6/2002 |
| WO | WO0248165 R4 | 6/2002 |
| WO | WO0248165 R5 | 6/2002 |
| WO | WO0248172 A2 | 6/2002 |
| WO | WO0248172 A3 | 6/2002 |
| WO | WO0248172 R4 | 6/2002 |
| WO | WO02048157 A3 | 6/2002 |
| WO | WO02048165 A3 | 6/2002 |
| WO | 02057287 | 7/2002 |
| WO | WO02057425 A2 | 7/2002 |
| WO | WO02060926 A2 | 8/2002 |
| WO | WO02060926 A3 | 8/2002 |
| WO | 02/100415 A2 | 12/2002 |
| WO | WO02100415 A3 | 12/2002 |
| WO | WO02100415 R4 | 12/2002 |
| WO | WO02108415 A2 | 12/2002 |
| WO | WO03024461 A1 | 3/2003 |
| WO | WO 03/051899 | 6/2003 |
| WO | 03/061576 A2 | 7/2003 |
| WO | WO 03/053989 | 7/2003 |
| WO | WO 03/062256 | 7/2003 |
| WO | WO 03/068244 | 8/2003 |
| WO | 03/105770 A2 | 12/2003 |
| WO | WO 03/106477 | 12/2003 |
| WO | WO2004000858 A2 | 12/2003 |
| WO | WO2004000858 A3 | 12/2003 |
| WO | WO2004000858 R4 | 12/2003 |
| WO | 2004/002422 A2 | 1/2004 |
| WO | 2004/009020 A2 | 1/2004 |
| WO | 2004007512 | 1/2004 |
| WO | WO 2004/009610 | 1/2004 |
| WO | WO2004002999 A2 | 1/2004 |
| WO | WO2004002999 A3 | 1/2004 |
| WO | WO2004002999 R4 | 1/2004 |
| WO | WO2004003000 A2 | 1/2004 |
| WO | WO2004003000 A3 | 1/2004 |
| WO | WO2004003000 R4 | 1/2004 |
| WO | WO2004003138 A2 | 1/2004 |
| WO | WO 2004/011478 | 2/2004 |
| WO | WO 2004/080466 | 9/2004 |
| WO | WO 2004/096234 | 11/2004 |
| WO | WO 2004/096235 | 11/2004 |
| WO | WO 2004/096286 | 11/2004 |
| WO | WO 2004/106356 | 12/2004 |
| WO | WO 2005/002626 | 1/2005 |
| WO | WO 2005/003147 | 1/2005 |
| WO | WO 2005/007810 | 1/2005 |
| WO | WO 2005008877 | 1/2005 |
| WO | WO 2005/009418 | 2/2005 |
| WO | WO 2005/012327 | 2/2005 |
| WO | WO 2005/020884 | 3/2005 |
| WO | WO 2005/021568 | 6/2005 |
| WO | WO 2005/072361 | 8/2005 |
| WO | WO 2006/000922 | 1/2006 |
| WO | 2006012440 | 2/2006 |
| WO | WO2006/012440 | 2/2006 |
| WO | WO 2006/029081 | 3/2006 |
| WO | WO 2006/031725 | 3/2006 |
| WO | WO 2006/037028 | 4/2006 |
| WO | WO 2006/061576 | 6/2006 |
| WO | WO 2006/065335 | 6/2006 |

OTHER PUBLICATIONS

Sun Xao-Ling and Wu Yu-Lin "The Synthesis of (2S,3R)-Sphingosine from D-Mannitol", Acta Chimica Sinica, 1996, vol. 54, pp. 826-832.

U.S. Appl. No. 60/392,350, filed May 21, 2001, Elek.

U.S. Appl. No. 60/392,351, filed Jun. 28, 2002, Storer.

Battaglia, A. et al., "Combination Therapy with Interferon and Ribavirin in the Treatment of Chronic Hepatitis C Infection," The Annals of Pharmacotherapy, vol. 34, No. 4, pp. 487-494 (Apr. 2000).

Berenguer, M. et al., "Hepatitis C virus in the transplant setting," Antiviral Therapy. Second International Conference on Therapies for Viral Hepatitis, vol. 3, Supplement 3, pp. 125-136 (1998).

Bhat, B. et al., "Synthesis and Pharmacokinetic Properties of Nucleoside Analogues as Possible Inhibitors of HCV RNA Replication," (Oral Session V: Hepatitis C Virus, Flaviviruses), 16th International Conference on Antiviral Research, Abstract No. 120, p. A75 (Apr. 27-May 1, 2003, Savannah, GA).

Chu, M. et al., "Isolation and structure of Sch 351633: A novel hepatitis C virus (HCV) NS3 protease inhibitor from the fungus *Penicillium griseofulvum*," Bioorganic & Medicinal Chemistry Letters, vol. 9, pp. 1949-1952 (1999).

Chu, M. et al., "Structure of Sch 68631: A New Hepatitis C Virus Proteinase Inhibitor from *Streptomyces* sp.," Tetrahedron Letters, vol. 37, No. 40, pp. 7229-7232 (Sep. 30, 1996).

Clark, J. et al., "Design, Synthesis, and Antiviral Activity of 2'-Deoxy-2'-fluoro-2'-C-methylcytidine, a Potent Inhibitor of Hepatitis C Virus Replication," Journal of Medicinal Chemistry, vol. 48, No. 17, pp. 5504-5508 (2005).

Davis, G. L., "Current Therapy for Chronic Hepatitis C," Gastroenterology 118: S104-S114, 2000.

De Lombaert, S. et al., "N-Phosphonomethyl Dipeptides and their Phosphonate Prodrugs, a New Generation of Neutral Endopeptidase (NEP, EC 3.4.24.11) Inhibitors," J. Med. Chem., vol. 37, No. 4, pp. 498-511 (1994).

Edmundson et al., "Cyclic Organophophorus Compounds Part 23. Configurational Assignments in the 4-Phenyl-1,3,2 $\lambda^5$-dioxaphosphorinane Series. X-Ray Molecular Structure of cis-2-Benzylamino-4-phenyl-1,3,2-dioxaphosphorinane 2-Oxide," J. Chem. Res. Synop., 1989, 5:122.

Eldrup, A. et al., "Structure Activity Relationship of 2' Modified Nucleosides for Inhibition of Hepatitis C Virus," (Oral Session V: Hepatitis C Virus, Flaviviruses), 16th International Conference on Antiviral Research, Abstract No. 119, p. A75 (Apr. 27-May 1, 2003, Savannah, GA).

Eldrup, A. et al., "Structure-Activity Relationship of Purine Ribonucleosides for Inhibition of Hepatitis C Virus RNA-Dependent RNA Polymerase," J. Med. Chem., vol. 47, No. 9, pp. 2283-2295 (2004).

Farquhar, D. et al., "Synthesis and Biological Evaluation of Neutral Derivatives of 5-Fluoro-2'-deoxyuridine 5'-Phosphate," J. Med. Chem., vol. 26, No. 8, pp. 1153-1158 (Aug. 1983).

Freed, J. et al., "Evidence for acyloxymethyl esters of pyrimidine 5'-deoxyribonucleotides as extracellular sources of active 5'-deoxyribonucleotides in cultured cells," Biochemical Pharmacology, vol. 38, No. 19, pp. 3193-3198 (Oct. 1, 1989).
Farquhar, D. et al., "Synthesis of Biological Evaluation of 9-[5'-(2-Oxo-1,3,2-oxazaphosphorinan-2-yl)-β-D-arabinosyl]adenine: Potential Nuetral Precursors of 9-[β-D-Arabinofuranosyl]adenine 5'-Monophosphate," J. Med. Chem., vol. 28, No. 9, pp. 1358-1361 (Sep. 1985).
Hertel, et al. "Synthesis of 2-Deoxy-2,2-difluoro-D-ribose and 2-Deoxy-2,2-difluoro-D-ribofuranosyl Necleosides," J. Org. Chem. vol. 53, pp. 2406-2409, (1988).
Hostetler, K. et al., "Greatly Enhanced Inhibition of Human Immunodeficiency Virus Type 1 Replication in CEM and HT4-6C Cells by 3'-Deoxythymidine Diphosphate Dimyristoylglycerol, a Lipid Prodrug of 3'-Deoxythymidine," Antimicrob. Agents Chemother., vol. 36, No. 9, pp. 2025-2029 (Sep. 1992).
Hostetler, K. et al., "Synthesis and Antiretroviral Activity of Phospholipid Analogs of Azidothymidine and Other Antiviral Nucleosides," J. Biol. Chem., vol. 265, No. 11, pp. 6112-6117 (Apr. 15, 1990).
Hunston, R. et al., "Synthesis and Biological Properties of Some Cyclic Phosphotriesters Derived from 2'-Deoxy-5-fluorouridine," J. Med. Chem., vol. 27, No. 4, pp. 440-444 (Apr. 1984).
International Search Report and Opinion for International Application No. PCT/US05/25916.
Jones, R. et al., "Minireview: Nucleotide prodrugs," Antiviral Research, vol. 27, pp. 1-17 (1995).
Khamnei, S. et al., "Neighboring Group Catalysis in the Design of Nucleotide Prodrugs," J. Med. Chem., vol. 39, No. 20, pp. 4109-4115 (1996).
Kotra, L.P., "Structure-Activity Relationships of 2'-Deoxy-2',2'-difluoro-L-erythro-pentofuranosyl Nucleosides," J. Med. Chem., vol. 40, pp. 3635-3644, (1997).
Kryuchkov, A. et al., "Influence of Solvent on the Strength of Cyclic Oxygen-Containing Phosphorus Acids," Bulletin of the Academy of Sciences of the USSR. Division of Chemical Science, vol. 36, No. 6, Part 1, pp. 1145-1148 (1987).
Meier, C. et al., "Cyclic Saligenyl Phosphotriesters of 2',3'-Dideoxy-2',3'-didehydrothymidine (d4T)—A New Pro-Nucleotide Approach," Bioorganic & Medicinal Chemistry Letters, vol. 7, No. 2, pp. 99-104 (1997).
Mitchell, A. et al., "Bioreversible Protection for the Phospho Group: Bioactivation of the Di(4-acyloxybenzyl) and Mono(4-acyloxybenzyl) Phosphoesters of Methylphosphonate and Phosphonoacetate," Journal of the Chemical Society, Perkin Transactions 1, No. 18, pp. 2345-2353 (Sep. 21, 1992).
Neidlein, R. et al., "Mild preparation of 1-benzyloxyminoalkylphosphonic dichlorides: Application to the synthesis of cyclic phosphonic diesters and cyclic monoester amides," Heterocycles, vol. 35, No. 2, pp. 1185-1203 (1993).
Nifantyev, E. et al., "Synthesis and structure of some stable phospholane-phospholanes," Phosphorus, Sulfur, and Silicon and the Related Elements, vol. 113, pp. 1-13 (1996).
Olsen, D. et al., "2'-Modified Nucleoside Analogs as Inhibitors of Hepatitis C RNA Replication," (Oral Session V: Hepatitis C Virus, Flaviviruses), 16th International Conference on Antiviral Research, Abstract No. 121, p. A76 (Apr. 27-May 1, 2003, Savannah, GA)).
Piantadosi, C. et al., "Synthesis and Evaluation of Novel Ether Lipid Nucleoside Conjugates for Anti-HIV-1 Activity,", J. Med. Chem., vol. 34, No. 4, pp. 1408-1414 (1991).
Shih, Y. et al., "Preparation and Structures of 2-Dimethylamino-4-phenyl-1,3,2-dioxaphosphorinane-2-oxides," Bull. Inst. Chem. Academia Sinica, No. 41, pp. 9-16 (Mar. 1994).
Starrett, Jr., J. et al., "Synthesis, Oral Bioavailability Determination, and in Vitro Evaluation of Prodrugs of the Antiviral Agent 9-[2-(Phosphonomethoxy)ethyl]adenine (PMEA)," J. Med. Chem., vol. 37, No. 12, pp. 1857-1864 (1994).
Stuyver, L. et al., "Dynamics of Subgenomic Hepatitis C Virus Replicon RNA Levels in Huh-7 Cells after Exposure to Nucleoside Antimetabolites," Journal of Virology, vol. 77, No. 19, pp. 10689-10694 (Oct. 2003).
Stuyver, L. et al., "Inhibition of the Subgenomic Hepatitis C Virus Replicon in Huh-7 Cells by 2'-Deoxy-2'- fluorocytidine," Antimicrob. Agents Chemother., vol. 48, No. 2, pp. 651-654 (Feb. 2004).
Stuyver, L. et al., "Ribonucleoside Analogue that Blocks Replication of Bovine Viral Diarrhea and Hepatitis C Viruses in Culture," Antimicrob. Agents Chemother., vol. 47, No. 1, pp. 244-254 (Jan. 2003).
Zon, G., "4 Cyclophosphamide Analogues," Progress in Medicinal Chemistry, vol. 19, pp. 205-246 (1982).
Novak, J.J.K. et al., "Nucleic Acid Components and Their Analogs. CXLIII. Nucleosides Derived from 2-Deoxy-2(R)-C-Methyl-Erythro-D-Pentose," Collection of Czechoslovak Chemical Communications, vol. 36, pp. 3670-3677 (1971).
Novak, J.J.K. et al., "Chiroptical Properties of 2-Methyl-1,4-Lactones; Revised Absolute Configuration of 2-Deoxy-2-C-Methyl-Erythro- D-Pentono-1,4-Lactones," Collection of Czechoslovak Chemical Communications, vol. 39, pp. 869-882 (1974).
Oishi, T. et al., Asymmetric dihydroxylation of chiral olefins. High control of diastereofacial selection, 34 Tetrahedron Letters, pp. 3573-3576 (1993).
Hernandez, R. et al., Synthesis of highly functionalized chiral nitriles by radical fragmentation of beta-hydroxy azides. Convenient transformation of aldononitriles into 1,4- and 1,5-iminoalditols. 69 J. Org. Chem., pp. 8437-8444 (2004).
Pending U.S. Appl. No. 12/786,459, filed May 25, 2010.
Kryuchkov, AA, et al, "Influence of Solvent on the Strength of Cyclic Oxygen-Containing Phosphorus Acid," 36 Bull. Acad. Sciences of the USSR, Division of Chemical Science, pp. 1145-1148 (1987).
Kotra et al., 40 J. Med. Chem., 3635-3644 (1997).
Fuentes et al., 319 Carbohydrate Research, 192-198 (1999).
Fuentes et al., 39 Tetrahedron Letters, 7149-7152 (1998).
Sun et al., 54 Huaxue Xuebao, 826-832 (1996)—Abstract in English.
Notice of Rejection dated Jul. 5, 2011 from the Japanese Patent Office in connection with corresponding Japanese Patent App. No. 2007-532391.
Notice of Rejection dated Jul. 5, 2011 from the Japanese Patent Office in connection with corresponding Japanese Patent App. No. 2007-522763.
Legters et al., "A convenient synthesis of asiridine-2-cargoxylic esters", 111 Racueil des Travaux Climiques des Pays-Bas, pp. 1-15 (1992).
Murakami et al., "A stereoselective synthesis of 2-amino-2-deoxy-D-rebose", 11 Chemistry Letters, pp. 1271-1274 (1982).
Ballesteros, "Reaction of 2,3-O-isopropylidene-D-glyceraldehyde with carboxyl group-containing active methylene compounds. Configuration of the reaction products and preparation of 1-deoxyhexosws", 26 Rev. Soc. Quim. Mex., pp. 86-91 (1982)—Spanish.
Yamamoto et al., "Stereoselective synthesis of 2-amino-2-deoxy-D-arabinos and 2-deoxy-D-regose", 49 Agric. Biol. Chem., pp. 1435-1439 (1985).
Crey et al., "Deoxyribonolactone Lesion in DNA: Synthesis of Fluorinated Analogues", 22 Nucleosides, Nucleotides and Nucleic Acids, pp. 1093-1095 (2003).
Terada et al., "Stereo-modulating catalysts by europium(III) complexes in aldol reactions of chiral of α-alkoxy with ketene silyl acetals", 21 Chemistry Letters. pp. 29-32 (1992).
Welch et al., "A short synthesis of 2-deoxy-2-fluoro-ribo-D-pentopyranose", 4 J. Chem. Soc. Chem. Comm., pp. 186-188 (1985).
Shono et al., "Diastereoselective addition of electrogenerated trichloromethyl and dichloro(methoxycarbonyl)methyl anions to α-branching aldehydes", 106 J. Am. Chem. Soc., pp. 259-260 (1984).
Bois, et al., "Hydroxymethylation of aldonolactones and a chemical synthesis of 3-deoxy-3-fluoro-D-fructose", 253 Carbohydrate Research, pp. 196-206 (1997).
Sun et al., "Synthesis of (2S,3R)-sphingosine from D-mannitol", 54 Acta Chimica Sinica, pp. 826-832 (1996).
International Search Report and Written Opinion of the International Searching Authority issued in International Application No. PCT/US2005/025916, mailed Jun. 15, 2006.

International Search Report and Written Opinion of the International Searching Authority issued in International Application No. PCT/US2005/032406, mailed May 8, 2008.

Hong, J.H. et al., "Synthesis of novel 3'-C-methyl-apionucleosides: an asymmetric construction of a quaternary carbon by Claisen rearrangement," Carbohydrate Research, vol. 328, pp. 37-48 (2000).

Gakhokidze, R.A. et al., "Synthesis of alpha-D-Glucosaccharinic Acid Derivatives," Khimicheskaya, vol. 16, No. 2, pp. 115-20 (1990).

Geokjian, et al., "Synthesis of Fluorinated Macrocyclic Bis(indolyl)maleimides as Potential 19F NMR Probes for Protein Kinase C," J. Org. Chem., vol. 64, No. 12, pp. 4238-46 (1999).

Hara, O. et al., "Stereoselective Synthesis of the C13-C19 Fragment of the Cytotoxic Marine Products Calyculins; Part 2," Synlett., vol. 4, pp. 285-86 (1991).

Kita, Y. et al., "Chemistry of O-Silylated Ketene Acetals: Stereocontrolled Synthesis of 2-Deoxy- and 2-Deoxy-2-Calkyl-erythro-pentoses," J. Org. Chem., vol. 53, No. 3, pp. 554-61 (1988).

Kryuchkov, A.A., et al., "Influence of Solvent on the Strength of Cyclic Oxygen-Containing Phosphorus Acids," Bulletin of the Academy of Sciences of the USSR, Division of Chemical Science, Plenum Publishing Corp., vol. 36, No. 6, Part I, pp. 1145-1148 (Jun. 1987).

Banker, G.S. et al (Eds.), "Modern Pharmaceutics, 3rd ed.," p. 596 (Marcel Dekker, Inc., 1996).

Beers, M. H. et al. (Eds.), "The Merck Manual of Diagnosis and Therapy (17th ed.)," p. 379, col. 2- p. 380, col. 1, para. 1 (Merck Research Labs., 1999).

Li, N-S. et al., "Synthesis of the Phosphoramidite Derivative of 2'-Deoxy-2'-C-beta-methylcytidine," J. Org. Chem., vol. 68, pp. 6799-6802 (2003).

Lin, T-S. et al., " Synthesis of Several Pyrimidine L-Nucleoside Analogues as Potential Antiviral Agents," Tetrahedron, vol. 51, No. 4, pp. 1055-1068 (1995).

Lin, T-S. et al., "Design and Synthesis of 2', 3'-Dideoxy-2',3'-didehydro-beta-L-cytidine (beta-L-d4C) and 2',3'-Dideoxy-2',3'-didehydro-beta-L-5-fluorocytidine (beta-L-Fd4C), Two Exceptionally Potent Inhibitors of Human Hepatitis B Virus (HBV) and Potent Inhibitors of Human Immunodeficiency Virus (HIV) in vitro," J. Med. Chem., vol. 39, No. 9, pp. 1757-1759 (1996).

Locatelli, G. et al., "Hepatitis C Virus NS3 NTPase/Helicase: Different Stereoselectivity in Nucleoside Triphosphate Utilisation Suggests that NTPase and Helicase Activities are Coupled by a Nucleotide-dependent Rate Limiting Step," J. Mol. Biol., vol. 313, pp. 683-94 (2001).

Mangner, T. et al., "Synthesis of 2'-deoxy-2'[18F]fluoro-beta-D-arabinofuranosyl nucleosides, [18F]FAU, [18F]FMAU, [18F]FBAU and [18F]FBAU and [18F]FIAU, as potential PET agents for imaging cellular proliferation," Nuclear Med. and Biol., vol. 30, pp. 215-224 (Apr. 2003).

Manoharan, M. et al., "2'-O-and 3'O- Pyrimidine Aminotether-containing Oligonucleotides: Synthesis and Conjugation Chemistry," Tetrahedron Letters, vol. 36, No. 21, pp. 3647-50 (1995).

Marchand, A. et al., "Stereospecific synthesis of unnatural beta-L-enantiomers of 2-chloroadenine pentofuranonucleoside derivatives," J. Chem. Soc., Perkin Trans. 1, pp. 2249-2254 (1999).

T.W. Greene, et al., "Protective Groups in Organic Synthesis (3rd ed.)," pp. 14-17, 47-53 and 100-103 (John Wiley & Sons, Inc., 1999).

Verri, A. et al., "Relaxed enantioselectivity of human mitochondrial thymidine kinase and chemotherapeutic uses of L-nucleoside analogues," Biochem. J., vol. 328, pp. 317-320 (1997).

Von Janta-Lipinski M. et al., "Newly Synthesized L-Enantiomers of 3'-Fluoro-Modified beta-2'-Deoxyribonucleoside 5'-Triphosphates Inhibit Hepatitis B DNA Polymerases But Not the Five Cellular DNA Polymerases alpha, beta, gamma, delta, and epsilon Nor HIV-1 Reverse Transcriptase," J. Med. Chem., 41, No. 12, pp. 2040-2046 (1998).

Wolff, Manfred E. "Burger's Medicinal Chemistry and Drug Discovery, 5ed, Part I," pp. 975-977 (John Wiley & Sons, 1995).

International Search Report and Written Opinion of the International Searching Authority issued in International Application No. PCT/US2004/012472, mailed Dec. 30, 2004.

Canadian Office Action issued in corresponding application No. 2580457 dated Nov. 1, 2012.

Pinto, A.C. et al., "Selective conjugate addition of nitromethane to enoates derived from D-mannitol and L-tartaric acid," Tetrahedron: Asymmetry, vol. 13, pp. 1025-1031 (2002).

Lopez Aparicio, F.J et al., "The Knoevenagel-Doebner reaction in the synthesis of branched-chain sugar derivatives," Carbohydrate Research, vol. 103, pp. 158-164 (1982).

Lopez Aparicio, F.J. et al., "Synthesis of Saccharinic Acid Derivatives," Carbohydrate Research, vol. 129, pp. 99-109 (1984).

Kucera, L. et al., "Novel Membrane-Interactive Ether Lipid Analogs that Inhibit Infectious HIV-1 Production and Induce Defective Virus Formation," AIDS Research and Human Retroviruses, vol. 6, No. 4, pp. 491-501 (Apr. 1990).

* cited by examiner

PREPARATION OF 2'-FLUORO-2'-ALKYL-SUBSTITUTED OR OTHER OPTIONALLY SUBSTITUTED RIBOFURANOSYL PYRIMIDINES AND PURINES AND THEIR DERIVATIVES

CLAIM TO PRIORITY

This application claims priority to Provisional Patent Application Ser. No. 60/609,783, filed on Sep. 14, 2004, entitled "Preparation of 2'-Fluoro-2'-C-Alkyl- and Other Optionally Substituted Ribofuranosyl Pyrimidines and Purines," Provisional Patent Application Ser. No. 60/610,035, filed on Sep. 15, 2004, entitled "Preparation of 2'-Fluoro-2'-C-Alkyl- and Other Optionally Substituted Nucleosides," and Provisional Patent Application Ser. No. 60/666,230, filed Mar. 29, 2005, entitled "Synthesis of the Branched-Chain Nucleosides via Stereoselective Dihydroxylation of γ-Alkoxy-α,β-Unsaturated Esters," all of which are incorporated by reference in their entireties.

FIELD OF THE INVENTION

The present invention provides (i) processes for preparing a 2-deoxy-2-fluoro-2-methyl-D-ribonolactone derivatives, (ii) conversion of intermediate lactones to nucleosides with potent anti-HCV activity, and their analogues, and (iii) methods to prepare the anti-HCV nucleosides containing the 2'-deoxy-2'-fluoro-2'-C-methyl-β-D-ribofuranosyl nucleosides from a preformed, preferably naturally-occurring, nucleoside.

BACKGROUND OF THE INVENTION

HCV infection has reached epidemic levels worldwide, and has tragic effects on the infected patients. Presently there is no effective treatment for this infection and the only drugs available for treatment of chronic hepatitis C are various forms of alpha interferon (IFN-α), either alone or in combination with ribavirin. However, the therapeutic value of these treatments has been compromised largely due to adverse effects, which highlights the need for development of additional options for treatment.

HCV is a small, enveloped virus in the Flaviviridae family, with a positive single-stranded RNA genome of ~9.6 kb within the nucleocapsid. The genome contains a single open reading frame (ORF) encoding a polyprotein of just over 3,000 amino acids, which is cleaved to generate the mature structural and nonstructural viral proteins. ORF is flanked by 5' and 3' non-translated regions (NTRs) of a few hundred nucleotides in length, which are important for RNA translation and replication. The translated polyprotein contains the structural core (C) and envelope proteins (E1, E2, p7) at the N-terminus, followed by the nonstructural proteins (NS2, NS3, NS4A, NS4B, NS5A, NS5B). The mature structural proteins are generated via cleavage by the host signal peptidase. The junction between NS2 and NS3 is autocatalytically cleaved by the NS2/NS3 protease, while the remaining four junctions are cleaved by the N-terminal serine protease domain of NS3 complexed with NS4A. The NS3 protein also contains the NTP-dependent helicase activity which unwinds duplex RNA during replication. The NS5B protein possesses RNA-dependent RNA polymerase (RDRP) activity, which is essential for viral replication. Unlike HBV or HIV, no DNA is involved in the replication of HCV.

U.S. Patent Publication (US 2005/0009737 A1) discloses that 1-(2-deoxy-2-fluoro-2-C-methyl-β-D-ribofuranosyl)cytosine (14) is a potent and selective anti-HCV agent. Previously known synthetic procedures (Schemes 1-3) for this compound are quite inefficient, with very low overall yields and are not amendable to large-scale.

Scheme 1

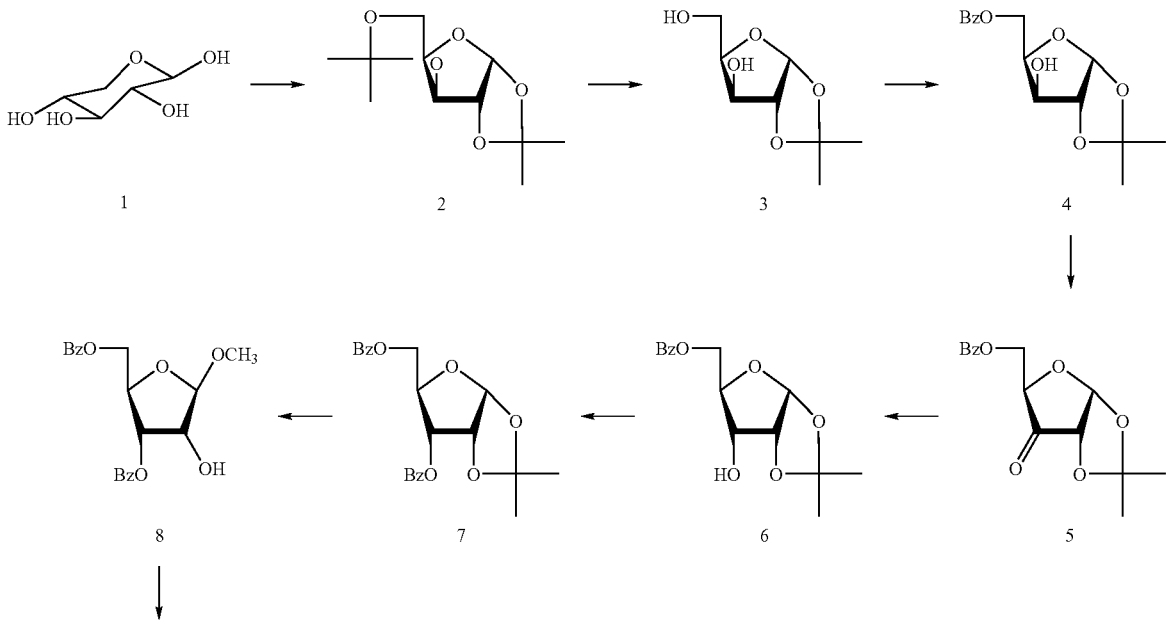

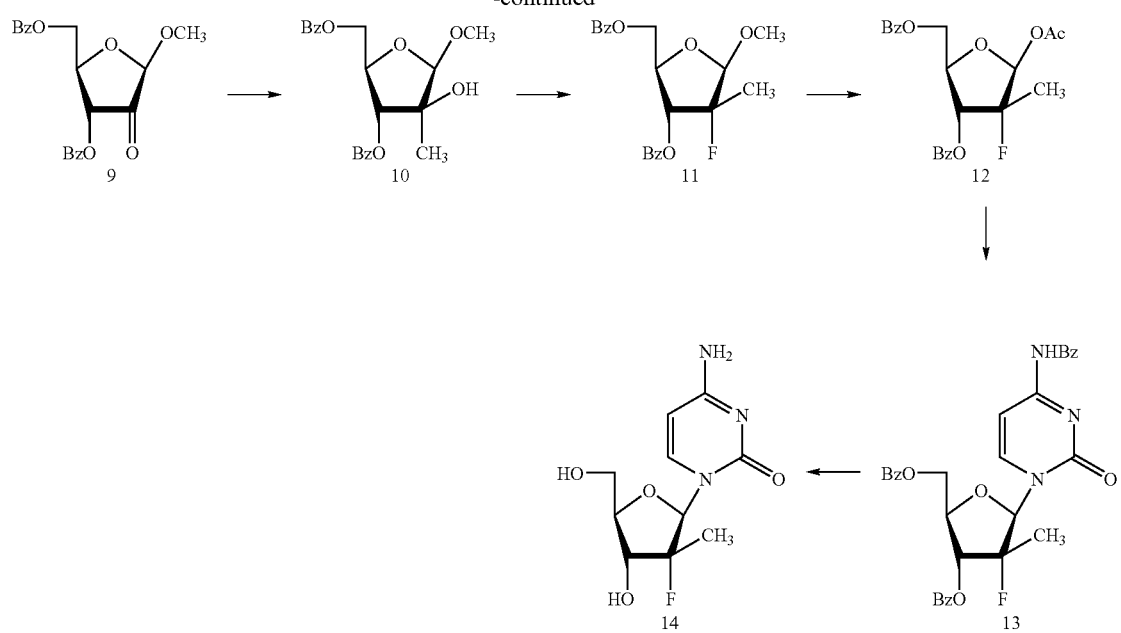
Scheme 2
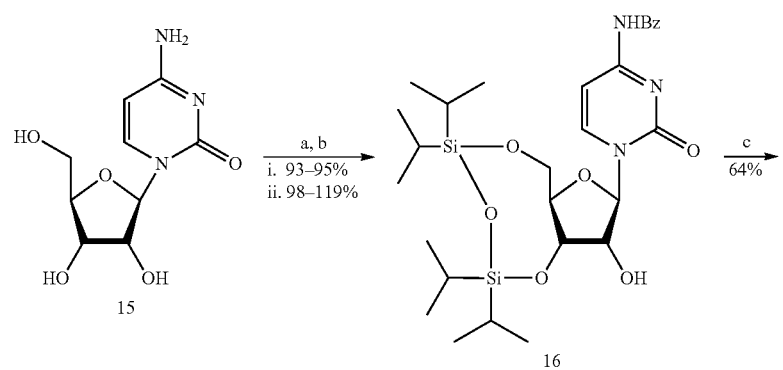
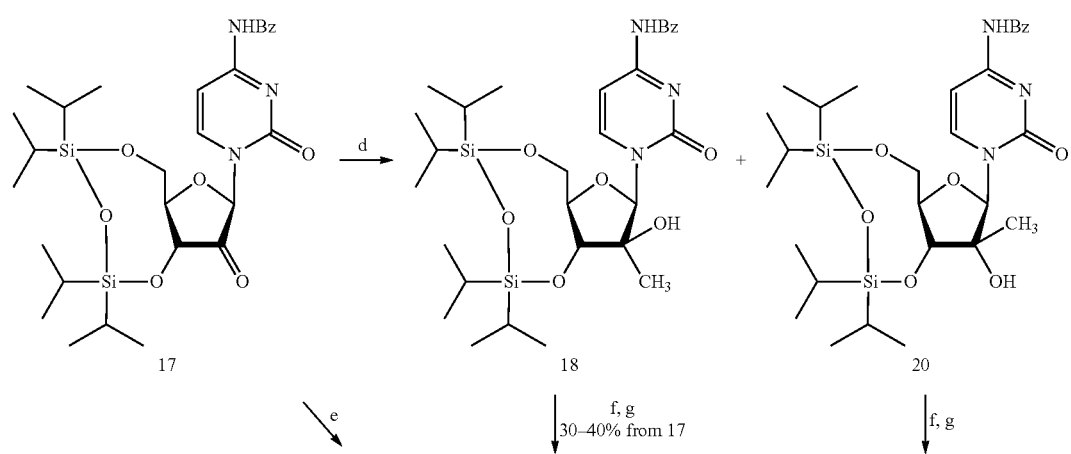

5
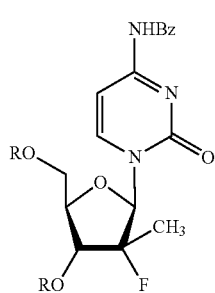
22
R = Ac, Bz
-continued
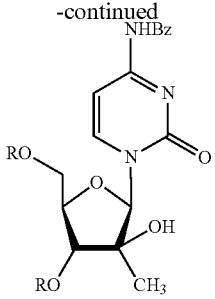
19
R = Ac, Bz
6
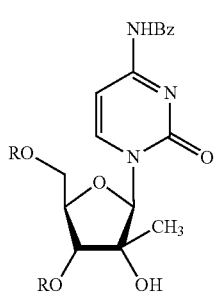
21
R = Ac, Bz
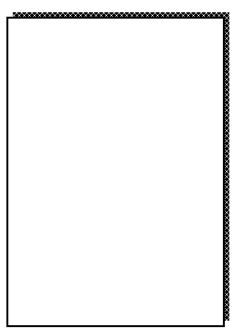
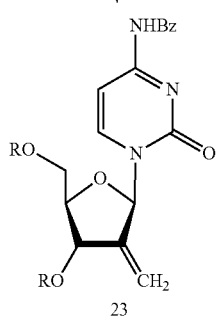
23
R = Ac, Bz
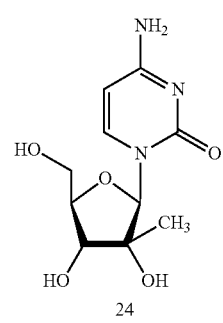
24
Reagents: a) Bz₂O/DMF; b) TIPDSCl₂/pyridine;
c) COCl₂/DMSO/-78° C.;
d) MeLi/Et₂O, -78° C.; e) MeMgBr/Et₂O; f) TBAF/THF;
g) BzCl/py; or Ac₂O/py; h) DAST/Toluene; i) NH₃/MeOH
Scheme 3
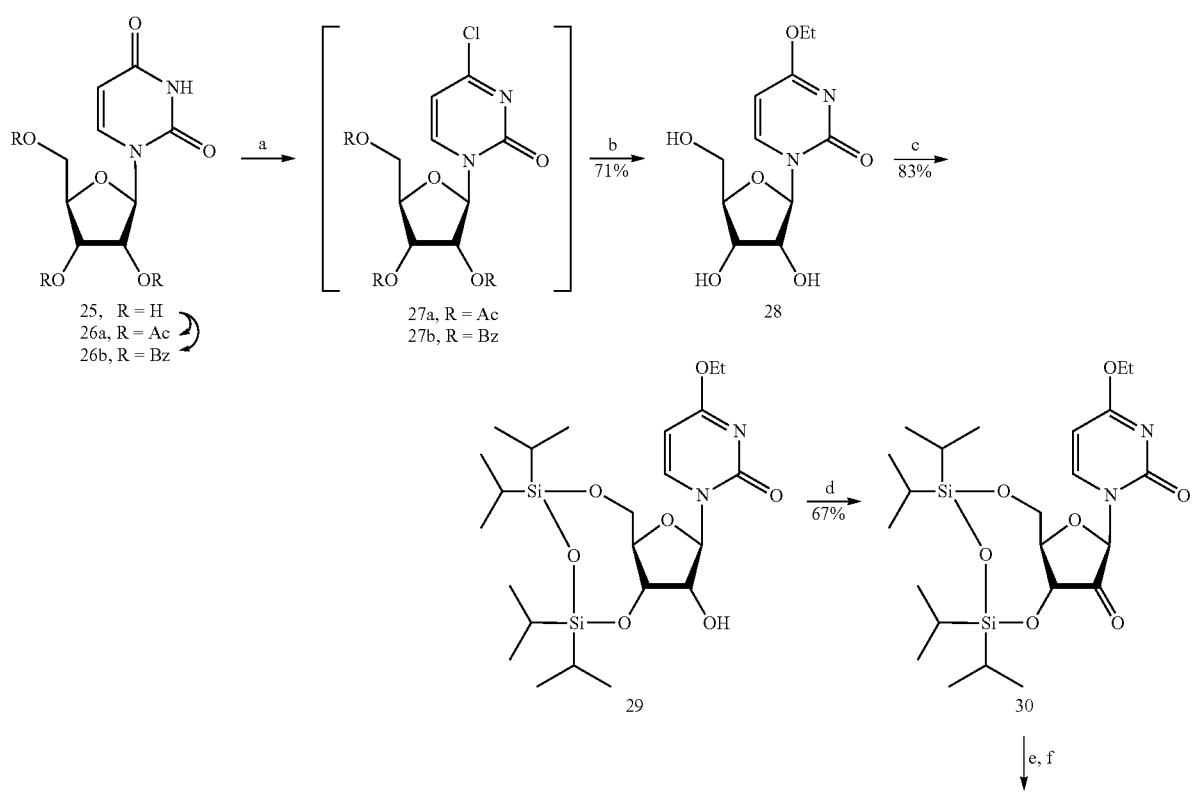

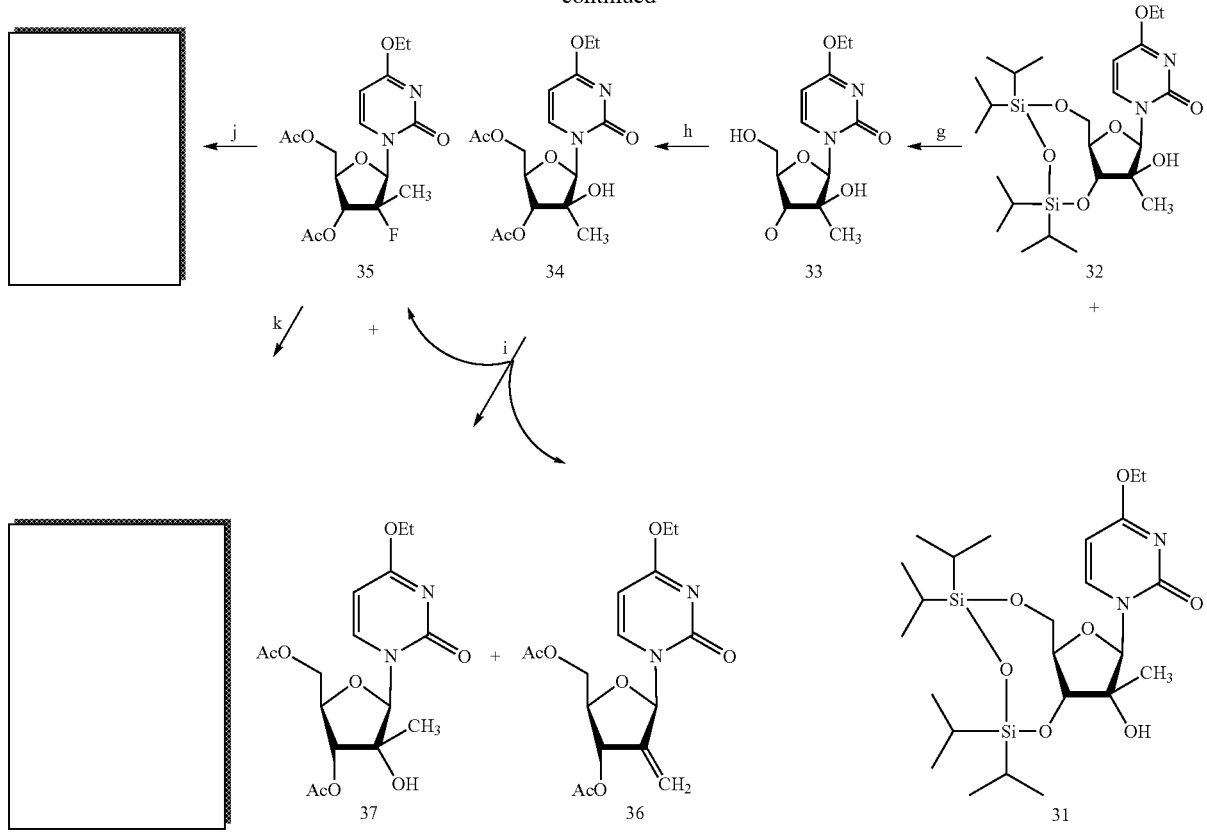

Reagents: a) SOCl$_2$/CH$_3$Cl, reflux; b) NaOEt/EtOH/reflux; c) TIPSDSCl$_2$/pyridin/rt; d) CrO$_3$/Ac$_2$O/pyridine, rt; e) MeLi/Et$_2$O, -78° C.;
f) MeMgBr/Et$_2$O, -50° C.; g) TBAF/THF; h) Ac$_2$O/py; i) DAST/Toluene; j) NH$_3$/MeOH; k) 1N NaOH/THF/60° C.

Previously known methods for the preparation of (2'R)-2'-deoxy-2'-fluoro-2'-C-methyl nucleosides, and its analogues, from D-xylose, cytidine, or uridine employed DAST or Deoxofluor® for the key fluorination reaction. However, DAST and Deoxofluor® are expensive, hazardous for industrial synthesis, and provide often unreliable results. Therefore, these alkylaminosulfur trifluorides are not suitable for industrial production.

As a part of an effort to find better fluorination conditions, it has been discovered that opening of a cyclic sulfate with non-alkylaminosulfur trifluoride fluorinating agents is an excellent way to synthesize the anti-HCV nucleoside, (2'R)-2'-deoxy-2'-fluoro-2'-C-methylcytidine. In addition, it was discovered that this novel synthetic route can be adopted to other nucleosides including the anti-HCV nucleoside, D-2-deoxy-2-fluoro-cytidine (Devos, et al, U.S. Pat. No. 6,660,721), anti-HBV nucleosides, D and L-2',3'-didehydro-2',3'-dideoxy-2'-fluoro-nucleosides (Schinazi, et al, U.S. Pat. No. 6,348,587) (I and II, FIG. 3) as well as other 2'-substituted nucleosides such as D- and L-FMAU (Su, et al., *J Med. Chem.*, 1986, 29, 151-154; Chu, et al., U.S. Pat. No. 6,512,107).

What is needed is a novel and cost effective process for the synthesis of 2'-C-alkyl-2'-deoxy-2'-substituted-D-ribopyranosyl nucleosides that have activity against HCV.

SUMMARY OF INVENTION

The present invention as disclosed herein relates to various intermediates and synthetic methods for the preparation of compounds of general formulas [I] and [II],

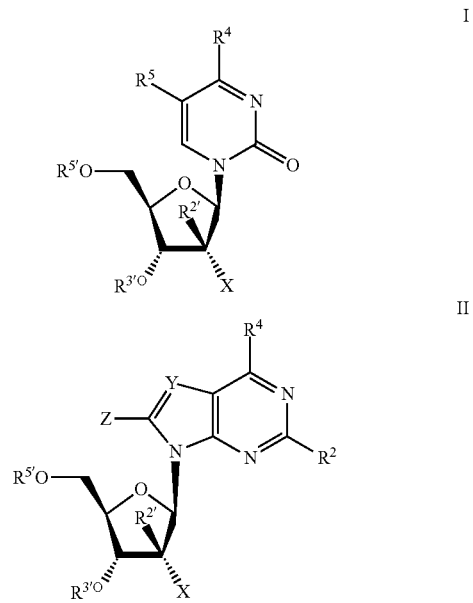

wherein
X is halogen (F, Cl, Br),
Y is N or CH,
Z is halogen, OH, OR' SH, SR', NH$_2$, NHR', or R'
R$^2$ is alkyl of C$_1$-C$_3$, vinyl, or ethynyl;

$R^{3'}$ and $R^{5'}$ can be same or different H, alkyl, aralkyl, acyl, cyclic acetal such as 2',3'-O-isopropylidene or 2',3-O-benzylidene, or 2',3'-cyclic carbonate.

$R^2$, $R^4$, and $R^5$ are independently H, halogen including F, Cl, Br, I, OH, OR', SH, SR', $N_3$, $NH_2$, NHR', $NR'_2$, NHC(O)OR', lower alkyl of $C_1$-$C_6$, halogenated (F, Cl, Br, I) lower alkyl of $C_1$-$C_6$ such as $CF_3$ and $CH_2CH_2F$, lower alkenyl of $C_2$-$C_6$ such as CH=$CH_2$, halogenated (F, Cl, Br, I) lower alkenyl of $C_2$-$C_6$ such as CH=CHCl, CH=CHBr and CH=CHI, lower alkynyl of $C_2$-$C_6$ such as C=CH, halogenated (F, Cl, Br, I) lower alkynyl of $C_2$-$C_6$, lower alkoxy of $C_1$-$C_6$ such as $CH_2OH$ and $CH_2CH_2OH$, halogenated (F, Cl, Br, I) lower alkoxy of $C_1$-$C_6$, $CO_2H$, $CO_2R'$, $CONH_2$, CONHR', $CONR'_2$, CH=$CHCO_2H$, CH=$CHCO_2R'$; and, R' is an optionally substituted alkyl or acyl of $C_1$-$C_{12}$ (particularly when the alkyl is an amino acid residue), cycloalkyl, optionally substituted alkynyl of $C_2$-$C_6$, optionally substituted lower alkenyl of $C_2$-$C_6$, or optionally substituted acyl.

DETAILED DESCRIPTION

Presently no preventive means against Flaviviridae, including hepatitis C virus (HCV), Dengue virus (DENV), West Nile virus (WNV) or Yellow Fever virus (YFV), infection is available. The only approved therapies are for treatment of HCV infection with alpha interferon alone or in combination with the nucleoside ribavirin, but the therapeutic value of these treatments has been compromised largely due to adverse effects. It was recently discovered that a group of nucleosides, including 2'-deoxy-2'-fluoro-2'-C-methylcytidine, exhibit potent and selective activity against replication of HCV in a replicon system. However, the difficulty of chemical synthesis of this and analogous nucleosides impedes further biophysical, biochemical, pharmacological evaluations mandatory for development of clinical drugs for treatment of Flaviviridae infection.

The present invention provides an efficient preparation of nucleosides and intermediates containing the 2-deoxy-2-fluoro-2-C-methyl-D-ribofuranosyl moiety.

DEFINITIONS

The term "independently" is used herein to indicate that the variable, which is independently applied, varies independently from application to application. Thus, in a compound such as $R^aXYR^a$, wherein $R^a$ is "independently carbon or nitrogen", both $R^a$ can be carbon, both $R^a$ can be nitrogen, or one $R^a$ can be carbon and the other $R^a$ nitrogen.

As used herein, the terms "enantiomerically pure" or "enantiomerically enriched" refers to a nucleoside composition that comprises at least approximately 95%, and preferably approximately 97%, 98%, 99% or 100% of a single enantiomer of that nucleoside.

As used herein, the terms "substantially free of" or "substantially in the absence of" refers to a nucleoside composition that includes at least 85 or 90% by weight, preferably 95% to 98% by weight, and even more preferably 99% to 100% by weight, of the designated enantiomer of that nucleoside. In a preferred embodiment, in the methods and compounds of this invention, the compounds are substantially free of enantiomers.

The term "alkyl," as used herein, unless otherwise specified, refers to a saturated straight or branched hydrocarbon chain of typically $C_r$ to $C_{10}$, and specifically includes methyl, ethyl, propyl, isopropyl, butyl, isobutyl, t-butyl, pentyl, isopentyl, neopentyl, hexyl, isohexyl, cyclohexyl, cyclohexylmethyl, 3-methylpentyl, 2,2-dimethylbutyl, and 2,3-dimethylbutyl, and the like. The term includes both substituted and unsubstituted alkyl groups. Alkyl groups can be optionally substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate. One or more of the hydrogen atoms attached to carbon atom on alkyl may be replaced by one or more halogen atoms, e.g. fluorine or chlorine or both, such as trifluoromethyl, difluoromethyl, fluorochloromethyl, and the like. The hydrocarbon chain may also be interrupted by a heteroatom, such as N, O or S.

The term "lower alkyl," as used herein, and unless otherwise specified, refers to a $C_1$ to $C_4$ saturated straight or branched alkyl group, including both substituted and unsubstituted forms as defined above. Unless otherwise specifically stated in this application, when alkyl is a suitable moiety, lower alkyl is preferred. Similarly, when alkyl or lower alkyl is a suitable moiety, unsubstituted alkyl or lower alkyl is preferred.

The term "cycloalkyl", as used herein, unless otherwise specified, refers to a saturated hydrocarbon ring having 3-8 carbon atoms, preferably, 3-6 carbon atoms, such as cyclopropyl, cyclobutyl, cyclopentyl and cyclohexyl. The cycloalkyl group may also be substituted on the ring by an alkyl group, such as cyclopropylmethyl and the like.

The terms "alkylamino" or "arylamino" refer to an amino group that has one or two alkyl or aryl substituents, respectively.

The term "protected," as used herein and unless otherwise defined, refers to a group that is added to an oxygen, nitrogen, or phosphorus atom to prevent its further reaction or for other purposes. A wide variety of oxygen and nitrogen protecting groups are known to those skilled in the art of organic synthesis. Non-limiting examples include: C(O)-alkyl, C(O)Ph, C(O)aryl, $CH_3$, $CH_2$-alkyl, $CH_2$-alkenyl, $CH_2Ph$, $CH_2$-aryl, $CH_2O$-alkyl, $CH_2O$-aryl, $SO_2$-alkyl, $SO_2$-aryl, tert-butyldimethylsilyl, tert-butyldiphenylsilyl, and 1,3-(1,1,3,3-tetraisopropyldisiloxanylidene).

The teem "aryl," as used herein, and unless otherwise specified, refers to phenyl, biphenyl, or naphthyl, and preferably phenyl. The term includes both substituted and unsubstituted moieties. The aryl group can be substituted with one or more substituents, including, but not limited to hydroxyl, halo, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in T. W. Greene and P. G. M. Wuts, "Protective Groups in Organic Synthesis," 3rd ed., John Wiley & Sons, 1999.

The terms "alkaryl" or "alkylaryl" refer to an alkyl group with an aryl substituent. The terms "aralkyl" or "arylalkyl" refer to an aryl group with an alkyl substituent, as for example, benzyl.

The term "halo," as used herein, includes chloro, bromo, iodo and fluoro.

The term "acyl ester" or "O-linked ester" refers to a carboxylic acid ester of the formula C(O)R' in which the non-carbonyl moiety of the ester group, R', is a straight or branched alkyl, or cycloalkyl or lower alkyl, alkoxyalkyl including methoxymethyl, aralkyl including benzyl, aryloxyalkyl such as phenoxymethyl, aryl including phenyl optionally substituted with halogen (F, Cl, Br, I), $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butyl silyl) or diphenylmethylsilyl. Aryl groups in the esters optimally include a phenyl group.

The term "acyl" refers to a group of the formula R"C(O)—, wherein R" is a straight or branched alkyl, or cycloalkyl, amino acid, aryl including phenyl, alkylaryl, aralkyl including benzyl, alkoxyalkyl including methoxymethyl, aryloxyalkyl such as phenoxymethyl; or substituted alkyl (including lower alkyl), aryl including phenyl optionally substituted with chloro, bromo, fluoro, iodo, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxy-trityl, substituted benzyl, alkaryl, aralkyl including benzyl, alkoxyalkyl including methoxymethyl, aryloxyalkyl such as phenoxymethyl. Aryl groups in the esters optimally comprise a phenyl group. In particular, acyl groups include acetyl, trifluoroacetyl, methylacetyl, cyclopropylacetyl, cyclopropyl carboxy, propionyl, butyryl, isobutyryl, hexanoyl, heptanoyl, octanoyl, neo-heptanoyl, phenylacetyl, 2-acetoxy-2-phenylacetyl, diphenylacetyl, α-methoxy-α-trifluoromethyl-phenylacetyl, bromoacetyl, 2-nitro-benzeneacetyl, 4-chloro-benzeneacetyl, 2-chloro-2,2-diphenylacetyl, 2-chloro-2-phenylacetyl, trimethylacetyl, chlorodifluoroacetyl, perfluoroacetyl, fluoroacetyl, bromodifluoroacetyl, methoxyacetyl, 2-thiopheneacetyl, chlorosulfonylacetyl, 3-methoxyphenylacetyl, phenoxyacetyl, tert-butylacetyl, trichloroacetyl, monochloro-acetyl, dichloroacetyl, 7H-dodecafluoro-heptanoyl, perfluoro-heptanoyl, 7H-dodeca-fluoroheptanoyl, 7-chlorododecafluoro-heptanoyl, 7-chloro-dodecafluoroheptanoyl, 7H-dodecafluoroheptanoyl, 7H-dodeca-fluoroheptanoyl, nona-fluoro-3,6-dioxa-heptanoyl, nonafluoro-3,6-dioxaheptanoyl, perfluoroheptanoyl, methoxybenzoyl, methyl 3-amino-5-phenylthiophene-2-carboxyl, 3,6-dichloro-2-methoxy-benzoyl, 4-(1,1,2,2-tetrafluoro-ethoxy)-benzoyl, 2-bromo-propionyl, omega-aminocapryl, decanoyl, n-pentadecanoyl, stearyl, 3-cyclopentyl-propionyl, 1-benzene-carboxyl, O-acetylmandelyl, pivaloyl acetyl, 1-adamantane-carboxyl, cyclohexane-carboxyl, 2,6-pyridinedicarboxyl, cyclopropane-carboxyl, cyclobutane-carboxyl, perfluorocyclohexyl carboxyl, 4-methylbenzoyl, chloromethyl isoxazolyl carbonyl, perfluorocyclohexyl carboxyl, crotonyl, 1-methyl-1H-indazole-3-carbonyl, 2-propenyl, isovaleryl, 1-pyrrolidinecarbonyl, 4-phenylbenzoyl. When the term acyl is used, it is meant to be a specific and independent disclosure of acetyl, trifluoroacetyl, methylacetyl, cyclopropylacetyl, propionyl, butyryl, isobutyryl, hexanoyl, heptanoyl, octanoyl, neo-heptanoyl, phenylacetyl, diphenylacetyl, ct-trifluoromethyl-phenylacetyl, bromoacetyl, 4-chloro-benzeneacetyl, 2-chloro-2,2-diphenylacetyl, 2-chloro-2-phenylacetyl, trimethylacetyl, chlorodifluoroacetyl, perfluoroacetyl, fluoroacetyl, bromodifluoroacetyl, 2-thiopheneacetyl, tert-butylacetyl, trichloroacetyl, monochloro-acetyl, dichloroacetyl, methoxybenzoyl, 2-bromo-propionyl, decanoyl, n-pentadecanoyl, stearyl, 3-cyclopentyl-propionyl, 1-benzene-carboxyl, pivaloyl acetyl, 1-adamantane-carboxyl, cyclohexane-carboxyl, 2,6-pyridinedicarboxyl, cyclopropane-carboxyl, cyclobutane-carboxyl, 4-methylbenzoyl, crotonyl, 1-methyl-1H-indazole-3-carbonyl, 2-propenyl, isovaleryl, 4-phenylbenzoyl.

The term "lower acyl" refers to an acyl group in which R", above defined, is lower alkyl.

The term "natural nucleic base" and "modified nucleic base" refer to "purine" or "pyrimidine" bases as defined below.

The term "purine" or "pyrimidine" base includes, but is not limited to, adenine, $N^6$-alkylpurines, $N^6$-acylpurines (wherein acyl is C(O)(alkyl, aryl, alkylaryl, or arylalkyl), $N^6$-benzylpurine, $N^6$-halopurine, $N^6$-vinylpurine, $N^6$-acetylenic purine, $N^6$-acyl purine, $N^6$-hydroxyalkyl purine, $N^6$-allylaminopurine, $N^6$-thioallyl purine, $N^6$-alkylpurines, $N^2$-alkyl-6-thiopurines, thymine, cytosine, 5-fluorocytosine, 5-methylcytosine, 6-azapyrimidine, including 6-azacytosine, 2- and/or 4-mercaptopyrimidine, uracil, 5-halouracil, including 5-fluorouracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $N^4$-acetylcytosine, $N^4$-benzoylcytosine, $N^4$-alkyl pyrimidine, $C^5$-hydroxyalkyl purine, $C^5$-amidopyrimidine, $C^5$-cyanopyrimidine, $C^5$-iodopyrimidine, $C^6$-iodo-pyrimidine, $C^5$-Br-vinyl pyrimidine, $C^6$-Br-vinyl pyrimidine, $C^5$-nitropyrimidine, $C^5$-amino-pyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, and pyrazolopyrimidinyl. Purine bases include, but are not limited to, guanine, adenine, hypoxanthine, 2,6-diaminopurine, and 6-chloropurine. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, trityl, alkyl groups, and acyl groups such as acetyl and propionyl, methanesulfonyl, and p-toluenesulfonyl.

The term "amino acid" includes naturally occurring and synthetic α, β γ or δ amino acids, and includes but is not limited to, amino acids found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In a preferred embodiment, the amino acid is in the L-configuration. Alternatively, the amino acid can be a derivative of alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleucinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl or β-histidinyl. When the term amino acid is used, it is considered to be a specific and independent disclosure of each of the esters of α, β γ or δ glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine in the D and L-configurations.

The term "pharmaceutically acceptable salt or prodrug" is used throughput the specification to describe any pharmaceutically acceptable form (such as an ester, phosphate ester, salt of an ester or a related group) of a compound which, upon administration to a patient, provides the active compound. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. Pharmaceutically acceptable salts may also be acid addition salts when formed with a nitrogen atom. Such salts are derived from pharmaceutically acceptable inorganic or organic acids, such as hydrochloric, sulfuric, phosphoric, acetic, citric, tartaric, and the like. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

Applicants have developed a novel, practical and efficient process for the synthesis of 2-C-alkyl-2-deoxy-2-substituted-D-ribofuranose derivatives, the key intermediates to 14 (Scheme 1) and derivatives and analogues thereof using or without using chiral catalysts. The key step in the synthesis of 14 is asymmetric conversion of 41 to 42 using chiral catalysts (Scheme 4). The previous disclosed synthesis of 42 required Sharpless AD catalysts, such as dihydroquinidine (DHQD) and derivatives. The present invention as disclosed herein relates to the stereoselective preparation of 41 to 42 using osmium, osmate or permanganate without chiral catalysts. The applicants in this present invention also develop a practical and efficient process for the synthesis of 49 from 42 by using the nucleophilic opening of the cyclic sulfate 50 (Scheme 6) in highly stereospecific and regioselective manner. The procedure depicted in Schemes 4, 5 and 6 are the current method of choice for preparative synthesis of 14 and related derivatives.

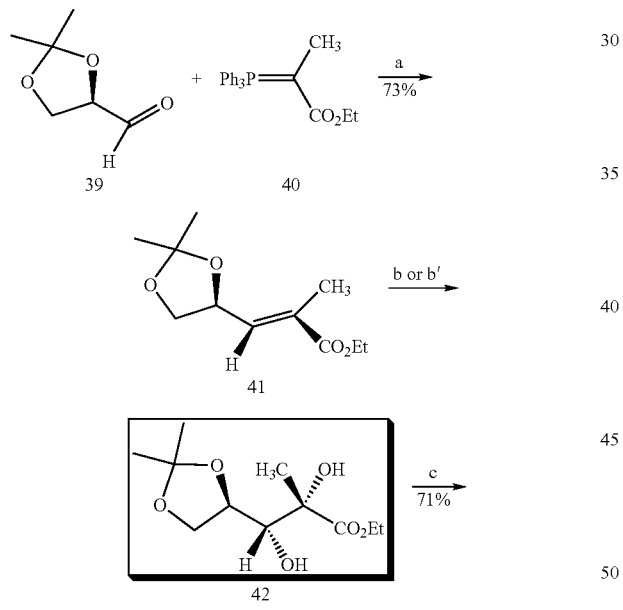

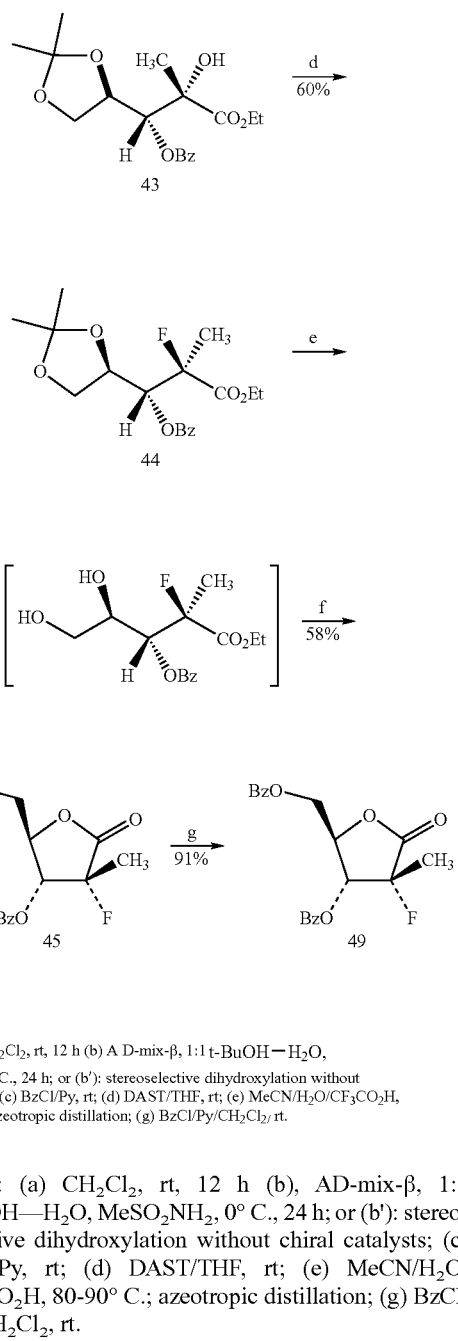

Reagent: (a) $CH_2Cl_2$, rt, 12 h (b) A D-mix-β, 1:1 t-BuOH—$H_2O$, $MeSO_2NH_2$, 0° C., 24 h; or (b'): stereoselective dihydroxylation without chiral catalysts; (c) BzCl/Py, rt; (d) DAST/THF, rt; (e) $MeCN/H_2O/CF_3CO_2H$, 80–90° C.; (f) azeotropic distillation; (g) BzCl/Py/$CH_2Cl_2$, rt.

Reagent: (a) $CH_2Cl_2$, rt, 12 h (b), AD-mix-β, 1:1 t-BuOH—$H_2O$, $MeSO_2NH_2$, 0° C., 24 h; or (b'): stereoselective dihydroxylation without chiral catalysts; (c) BzCl/Py, rt; (d) DAST/THF, rt; (e) $MeCN/H_2O/CF_3CO_2H$, 80-90° C.; azeotropic distillation; (g) BzCl/Py/$CH_2Cl_2$, rt.

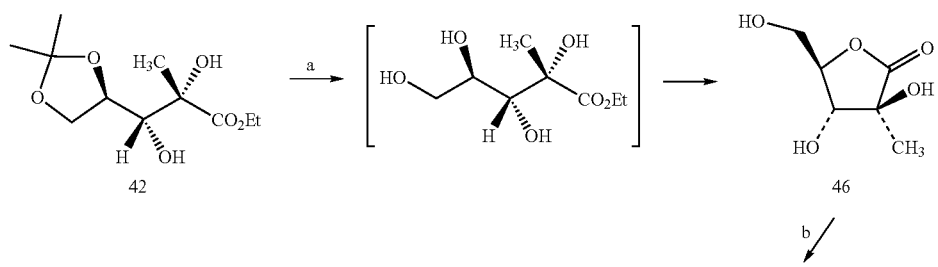

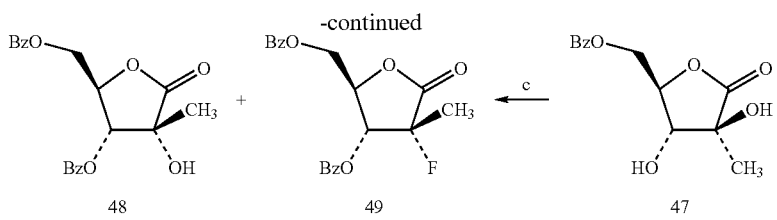

Reagent: (a) HCl/EtOH (b) BzClPy (c) DAST

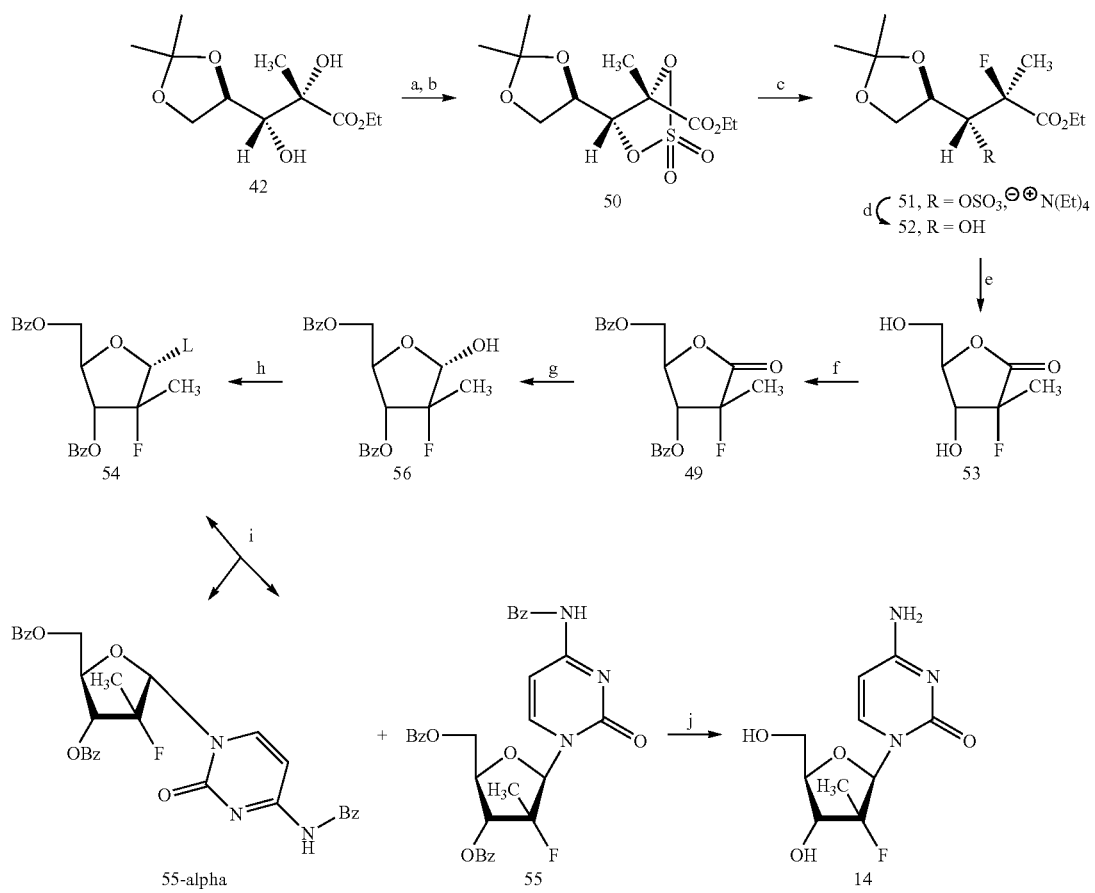

Reagent: (a) SOCl₂, Et₃N, CH₂Cl₂; (b) TEMPO-NaOCl, (c) TEAF (d) HCl (e) AcOH or Dowex-H⁺ (f) BzCl/Py; (g) LiAlOBu-t)₃H; (h) Ac₂O; (i) silylated bases/Vorbruggen condition; (j) NH₃/MeOH

I. Preparation of the Compounds

(i) Synthesis of the cyclic sulfite (IIIa) and cyclic sulfate (IIIb)

This invention relates to the process for the preparation of the 2'-F-nucleosides and other 2'-substituted nucleosides of the general formula IB and IB-L- by using the nucleophilic opening of the cyclic sulfite, Ma (X=SO), sulfate, IIIb (X=SO₂), of the formula, III in highly stereospecific and regioselective manner, via the lactones of the formula, IV.

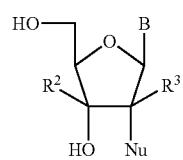

IB

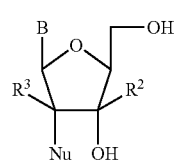

IB-L

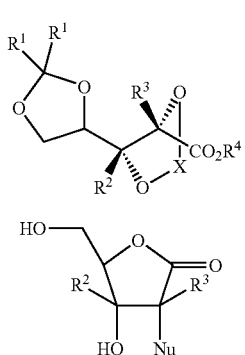

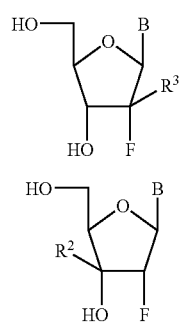

Wherein the formula IB, IB-L, III, IV has following specifications:

R¹ is independently a lower alkyl ($C_1$-$C_6$) including, but not limited to methyl, ethyl, optionally substituted phenyl, optionally substituted benzyl; alternatively R¹ is a part of cyclic alkylene including ethylene (—$CH_2CH_2$—), or trimethylene (—$CH_2CH_2CH_2$—) forming cyclic pentyl or cyclic hexanyl group;

$R^2$, $R^3$ are independently hydrogen, a lower alkyl ($C_1$-$C_6$) including, but not limited to methyl, hydroxymethyl, methoxymethyl, halomethyl including, but not limited to fluoromethyl, ethyl, propyl, optionally substituted ethenyl including, but not limited to vinyl, halovinyl (F—CH=C), optionally substituted ethynyl including, but not limited to haloethynyl (F—C≡C), optionally substituted allyl including, but not limited to haloallyl (FHC=CH—$CH_2$—);

$R^4$ is independently hydrogen, aryl including, but not limited to phenyl, aryl alkyl including, but not limited to benzyl, lower alkyl including, but not limited to, methyl, ethyl, propyl. Nu is halogen (F, Cl, Br), $N_3$, CN, $NO_3$, $CF_3$, OR or NR where R is acyl including, but not limited to acetyl, benzoyl, arylalkyl including but not limited to benzyl, lower alkyl including, but not limited to, methyl, ethyl, propyl, $CH_2R$ where R is hydrogen, lower alkyl including, but not limited to, methyl, ethyl, propyl;

X is $SO_2$, SO, or CO; and

B is a natural or modified nucleic base.

In one embodiment, formula, IB is:

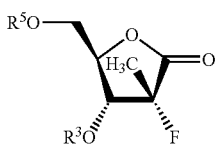

wherein, $R^2$, $R^3$ are independently hydrogen, a lower alkyl ($C_1$-$C_6$) including, but not limited to methyl, hydroxymethyl, methoxymethyl, halomethyl including, but not limited to fluoromethyl, ethyl, propyl, optionally substituted ethenyl including, but not limited to vinyl, halovinyl (F—CH=C), optionally substituted ethnyl including, but not limited to haloethnyl (F—C≡C), optionally substituted allyl including, but not limited to haloallyl (FHC=CH—$CH_2$—);

B is a natural or modified nucleic base.

The present invention as disclosed herein relates to processes for the synthesis of a compound, 2-alkyl-4,5-di-O-protected-2,3-dihydroxy-pentanoic-acid ester of the following general formula 42B, which is the important intermediate in the synthesis of anti-HCV nucleosides of general formulas [I] and [II] (below).

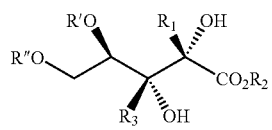

wherein R', R"=isopropylidene, benzylidene or cyclohexylidene or a like, or a part of cyclic group including ethylene (—$CH_2CH_2$—), or trimethylene (—$CH_2CH_2CH_2$—) forming cyclopentyl or cyclohexanyl group, respectively; R' and R" can be independently lower alkyl of $C_1$-$C_6$, or aryl of $C_6$-$C_{20}$), benzyl and other optionally substituted benzyl, trialkylsilyl, t-butyl-dialkylsyl, t-butyldiphenylsilyl, TIPDS, THP, MOM, MEM and other optionally ether protecting groups; or H, acetyl, benzoyl and other optionally substituted acyl (R' and R" are —C(O)—R, wherein R can be lower alkyl of $C_1$-$C_6$, or aryl of $C_6$-$C_{20}$, benzyl or other optionally substituted benzyl);

$R_1$, $R_2$ are independently hydrogen, aryl ($C_6$-$C_{20}$) and a lower alkyl ($C_1$-$C_6$) including methyl, hydroxymethyl, methoxymethyl, halomethyl including fluoromethyl, ethyl, propyl, optionally substituted ethenyl including vinyl, halovinyl (F—CH=C), optionally substituted ethynyl including haloethynyl (F—C≡C), optionally substituted allyl including haloallyl (FHC=CH—$CH_2$—); and $R_3$ is independently hydrogen, aryl including phenyl, aryl alkyl including, but not limited to benzyl, lower alkyl ($C_{1-6}$) including methyl, ethyl, or propyl.

The invention as disclosed herein also relates to processes for making compounds of the following general formula 49B, which are prepared from 2-alkyl-4,5-di-O-protected-2,3-dihydroxy-pentanoic-acid ester derivatives of general formula [42B].

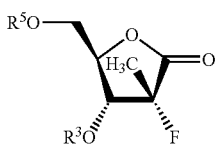

wherein $R^3$ and $R^5$ can be independently H, $CH_3$, Ac, Bz, pivaloyl, or 4-nitrobenzoyl, 3-nitrobenzoyl, 2-nitrobenzoyl, 4-chlorobenzoyl, 3-chlorobenzoyl, 2-chlorobenzoyl, 4-methylbenzoyl, 3-methylbenzoyl, 2-methylbenzoyl, para-phenylbenzoyl, and other optionally substituted acyl ($R^3$ and $R^5$ are —C(O)—R, R can be independently lower alkyl of $C_1$-$C_6$, or aryl of $C_6$-$C_{20}$), benzyl, 4-methoxybenzyl and other optionally substituted benzyl ($R^3$ and $R^5$ can be independently aryl of $C_6$-$C_{20}$), trityl, trialkylsilyl, t-butyl-dialkylsyl, t-butyl-diphenylsilyl, TIPDS, THP, MOM, MEM and other optionally ether protecting groups ($R^3$ and $R^5$ can be independently alkyl of $C_1$-$C_{10}$), or $R^3$ and $R^5$ are linked through —$SiR_2$—O—$SiR_2$— or —$SiR_2$—, wherein R is a lower alkyl group such as Me, Et, n-Pr or i-Pr.

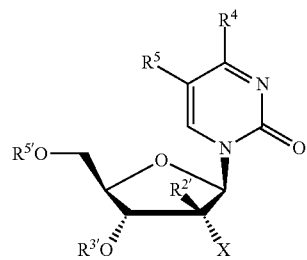

I

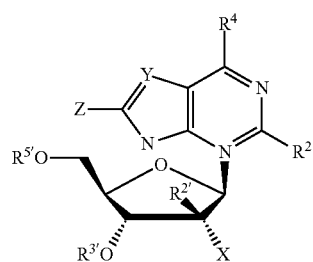

II wherein

X is halogen (F, Cl, Br),

Y is N or CH,

Z is, halogen, OH, OR', SH, SR', $NH_2$, NHR', or R'

$R^{2'}$ is alkyl of $C_1$-$C_3$, vinyl, or ethynyl $R^{3'}$ and $R^{5'}$ can be same or different H, alkyl, aralkyl, acyl, cyclic acetal such as 2',3'-O-isopropylidene or 2',3-O-benzylidene, or 2',3'-cyclic carbonate.

$R^2$, $R^4$, $R^5$ and $R^6$ are independently H, halogen including F, Cl, Br, I, OH, OR', SH, SR', $N_3$, $NH_2$, NHR', NR'', NHC(O)OR', lower alkyl of $C_1$-$C_6$, halogenated (F, Cl, Br, I) lower alkyl of $C_1$-$C_6$ such as $CF_3$ and $CH_2CH_2F$, lower alkenyl of $C_2$-$C_6$ such as CH=$CH_2$, halogenated (F, Cl, Br, I) lower alkenyl of $C_2$-$C_6$ such as CH=CHCl, CH=CHBr and CH=CHI, lower alkynyl of $C_2$-$C_6$ such as C≡CH, halogenated (F, Cl, Br, I) lower alkynyl of $C_2$-$C_6$, lower alkoxy of $C_1$-$C_6$ such as $CH_2OH$ and $CH_2CH_2OH$, halogenated (F, Cl, Br, I) lower alkoxy of $C_1$-$C_6$, $CO_2H$, $CO_2R'$, $CONH_2$, CONHR', $CONR'_2$, CH=$CHCO_2H$, CH=$CHCO_2R'$; and, R' and R'' are the same or different and are optionally substituted alkyl of $C_1$-$C_{12}$ (particularly when the alkyl is an amino acid residue), cycloalkyl, optionally substituted alkynyl of $C_2$-$C_6$, optionally substituted lower alkenyl of $C_2$-$C_6$, or optionally substituted acyl.

The reaction of the cyclic sulfate ester, 50 (Scheme 6) with tetraethylammonium fluoride or tetramethylammonium fluoride 51 (Scheme 6) quantitatively generated the fluorinated sulfate, in highly stereospecific and regioselective manner. Following acid catalyzed cyclization afforded the 2-fluoro-2-C-methyl-γ-ribonolactone, 53 in high yield. The present invention is based on this discovery and provides a process for the preparation of the T-deoxy-2'-substituted nucleosides, I and II, using the reactions described herein.

(2S,3R,4R)-4,5-O-alkylidene-2-dimethyl-2,3,4,5-tetrahydroxy-2-methyl-1-pentanoic acid ethyl ester (42B), can be prepared by asymmetric dihydroxylation (AD) or stereoselective dihydroxylation of the Wittig product 41 with or without chiral catalysts. Wittig product 41, in turn, can be prepared readily from the protected (R) glyceraldehyde (Schemes 7, 8), where $R^1$ is independently a lower alkyl ($C_1$-$C_6$) including, but not limited to methyl, ethyl, optionally substituted phenyl, optionally substituted benzyl. Or $R^1$ is a part of cyclic group including ethylene (—$CH_2CH_2$—), or trimethylene (—$CH_2CH_2CH_2$—) forming cyclopentyl or cyclohexanyl group, respectively. $R^2$, $R^3$ are independently hydrogen, a lower alkyl ($C_1$-$C_6$) including, but not limited to methyl, hydroxymethyl, methoxymethyl, halomethyl including, but not limited to fluoromethyl, ethyl, propyl, optionally substituted ethenyl including, but not limited to vinyl, halovinyl (F—CH=C), optionally substituted ethynyl including, but not limited to haloethynyl (F—C≡C), optionally substituted allyl including, but not limited to haloallyl (FHC=CH—$CH_2$—); and $R^4$ is acyl including, but not limited to acetyl, benzoyl, arylalkyl including but not limited to benzyl, lower alkyl ($C_{1-10}$) including, but not limited to, methyl, ethyl, propyl, $CH_2R$ where R is hydrogen, lower alkyl ($C_{1-10}$) including, but not limited to, methyl, ethyl, propyl.

Scheme 7

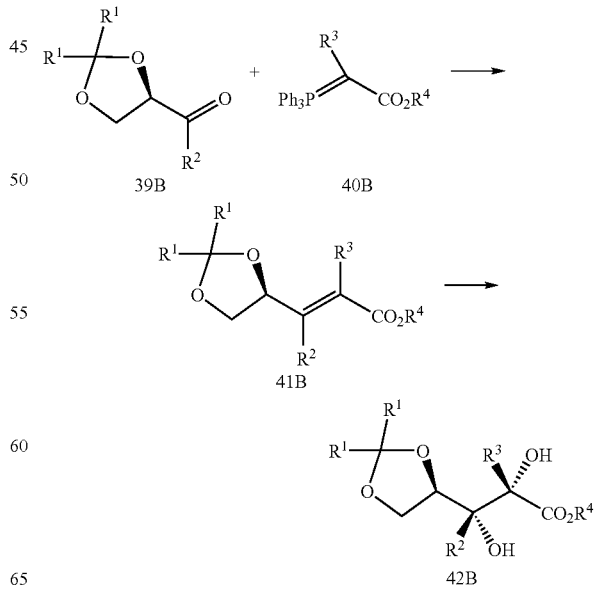

The diol (42B) can be converted to the cyclic sulfite (IIIa) by treatment with thionyl chloride (SOCl$_2$) in presence of an alkylamine such as triethylamine, diisopropyl ethylamine, or pyridine, which can then be oxidized using the oxidants selected from a first group consisting of RuCl$_3$, KMnO$_4$, and TEMPO or a combination of the first group and one of the second group consisting of NaIO$_4$, KIO$_4$, HIO$_4$, mCPBA, NaOCl, and oxone. The solvent of this step is selected from one or more of the group consisting of chloroform, methylene chloride, 1,2-dichloroethane, diethyl ether, tetrahydrofuran, benzene, and toluene, alone or in combination with water. (Gao Y et al *J. Am. Chem. Soc.* 1988, 110, 7538-7539, Berridge et al *J. Org. Chem.* 1990, 55, 1211-1217). It is also possible that the diol is directly converted to the cyclic sulfate (IIIb) by treatment with sulfurylchloride, or sulfuryl diimidazole. On the other hand, the diol 42B can be converted to the cyclic carbonate (IIIc) by treatment with carbonyl diimidazole or carbonyl dimethoxide (Scheme 8) (Chang, et al *Tetrahedron Lett.* 1996, 37, 3219-3222).

fluoride (AgF), potassium fluoride (KF), cesium fluoride (CsF), or rubidium fluoride (RbF), can be used alone or with catalytic amount of tetraalkylammonium fluoride, crown-ether, diglyme, or polyethylene glycol, or other phase transfer catalyst.

The cyclic sulfate (IIIb) can be converted to other 2-substituted sulfates of the formula 51B by treatment with NaBH$_4$, tetraalkylammonium chloride, tetraalkylammonium bromide, NaN$_3$ or LiN$_3$, NH$_4$OR, NH$_4$SCN, CF$_3$I-tetrakis(dimethylamino)-ethylene (TDAE), and tetraalkylammonium nitrate (Gao et al *J. Am. Chem. Soc.* 1988, 110, 7538-7539), KCN, LiCu(R)$_2$ where R is methyl, ethyl, ethylenyl, or ethynyl. Similarly, the cyclicsulfite (IIIa) can be converted to the substituted ester 52B (Chang et al. *Tetrahedron Lett.* 1996, 37, 3219-3222). Then compounds of the formula 51B and 52B can be converted to the substituted lactones of the formula 53B by treatment with an acid in H$_2$O-containing organic solvent such as methanol, ethanol, or acetonitrile.

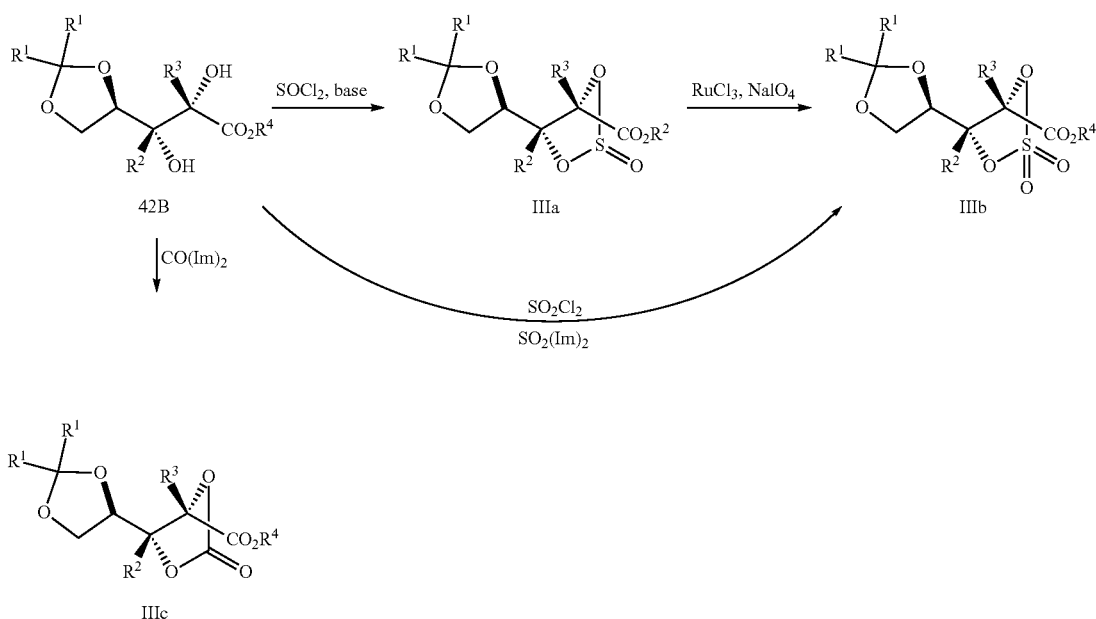

Scheme 8

(ii) Synthesis of the substituted 2-deoxy-D-ribono-γ-lactone, 53B

The cyclic sulfate (IIIb, Scheme 8) can be converted to the fluorinated sulfate ester of the formula, 51B (Scheme 9), in high yield and with high regioselectivity and stereospecificity, by treatment with tetraalkylammonium fluoride including, but not limited to tetramethylammonium fluoride (TMAF), tetraethylammonium fluoride (TEAF), or tetrabutylammomnium fluoride (TBAF), or tris(dimethylamino)sulfur (trimethylsilyl)difluoride (TAS-F) (Fuentes J, et al *Tetrahedron lett.* 1998, 39, 7149-7152) in an aprotic polar solvent such as acetone, tetrahydrofuran, N,N-dimethylformamide, or acetonitrile (Scheme 9). Metal fluorides such as silver In Formula 53B, R$^2$, R$^3$ is independently hydrogen, a lower alkyl (C$_1$-C$_6$) including, but not limited to methyl, hydroxymethyl, methoxymethyl, halomethyl including, but not limited to fluoromethyl, ethyl, propyl, optionally substituted ethenyl including, but not limited to vinyl, halovinyl (F—CH═C), optionally substituted ethynyl including, but not limited to haloethynyl (F—C≡C), optionally substituted allyl including, but not limited to haloallyl (FHC═CH—CH$_2$—). Nu is halogen (F, Cl, Br), N$_3$, CN, NO$_3$, CF$_3$, SCN, OR or NR$_2$ where R is acyl including, but not limited to acetyl, benzoyl, arylalkyl including but not limited to benzyl, lower alkyl (C$_{1-10}$) including, but not limited to methyl, ethyl, propyl, CH$_2$R where R is hydrogen, lower alkyl (C$_{1-10}$) including, but not limited to methyl, ethyl, propyl.

Scheme 9

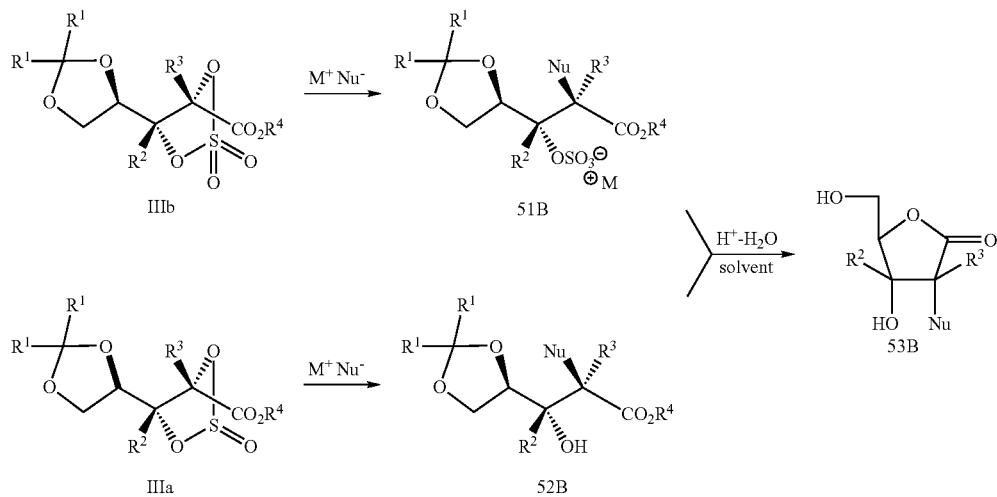

(iii) The Protection of the D-Ribono-γ-Lactone, 53B 53B can be selectively protected with appropriate protection agents to the 5-protected lactones of the formula 53C with an appropriate base in an appropriate solvent. The protecting group includes, but is not limited to the following: trityl, t-butyldimethylsilyl, t-butyldiphenylsilyl, benzyloxymethyl, benzoyl, toluoyl, 4-phenyl benzoyl, 2-, 3-, or 4-nitrobenzoyl, 2-, 3-, or 4-chlorobenzoyl, other substituted benzoyl. The base includes, but is not limited to the following: imidazole, pyridine, 4-(dimethylamino)pyridine, triethylamine, diisopropylethylamine, 1,4-diazabicyclo[2,2,2]-octane. The solvent includes, but is not limited to the following: pyridine, dichloromethane, chloroform, 1,2-dichloroethane, tetrahydrofuran.

Alternatively, the lactone 53B can be fully protected with appropriate protection agents with an appropriate base in an appropriate solvent. The protecting group ($R^5$, $R^6$) includes, but is not limited to the following: methoxymethyl, methoxyethyl, benzyloxymethyl, ethoxymethyl, trityl, triethylsilyl, t-butyldimethylsilyl, t-butyldiphenylsilyl, acyl including acetyl, pivaloyl, benzoyl, toluoyl, 4-phenyl benzoyl, 2-, 3-, or 4-nitrobenzoyl, 2-, 3-, or 4-chlorobenzoyl, other substituted benzoyl. The base includes, but is not limited to the following list: imidazole, pyridine, 4-(dimethylamino)pyridine, triethylamine, diisopropylethylamine, 1,4-diazabicyclo[2,2,2]octane. The solvent includes, but is not limited to pyridine, dichloromethane, chloroform, 1,2-dichloroethane, tetrahydrofuran (Scheme 10).

Scheme 10

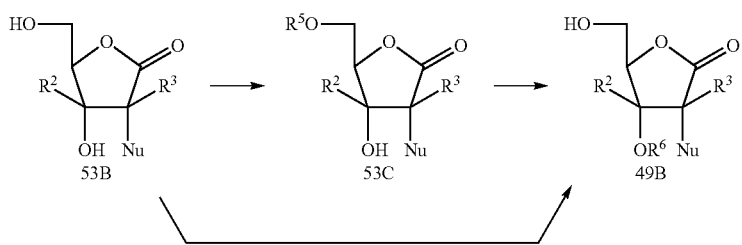

(ii) Complexation Directed β-Glycosylation

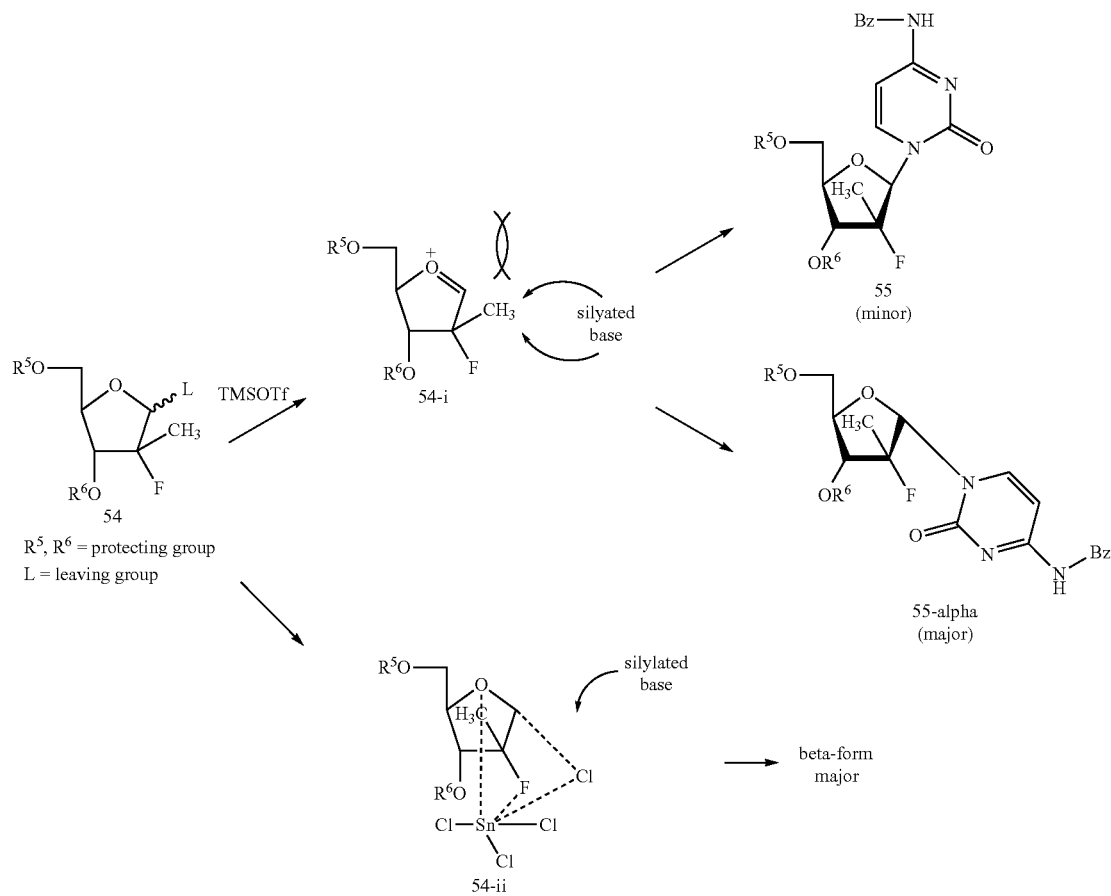

Scheme 10a

Coupling of 2-deoxy-2-fluoro-2-C-methyl-ribofuranoside (54: Nu=F, $R^3$=Me, $R^5$=$R^6$=pivaloyl) with silylated $N^4$-benzoylcytosine in the presence of trimethylsilyl trifluoromethanesulfonate (TMSOTf) in $CHCl_3$ gave a mixture of a/13-anomers with a ratio of 2/1 in favor of α-isomer. However, β-anomer was obtained as major product (α/β=1/4.9) in the same reaction catalyzed by $SnCl_4$ under similar conditions. Possible mechanisms are proposed in Scheme 10A ($R^5$ and $R^6$ are O-protecting groups that can be acyl or silyl or alkyl or aralkyl with $C_{1-20}$). Treatment of 54 with silylated $N^4$-benzoylcytosine in the presence of TMSOTf in $CHCl_3$ formed an oxonium intermediate 54-i. Silylated base could attack 54-1 from up-side to give β-anomer 55B or from bottom to provide α-anomer 55B-alpha. Because of stereohinderance at up-side caused by 2-methyl group, silylated base attacked intermediate 54-i mainly from bottom (less stereohindered side) to afford a mixture of α/β-anomers with a ratio of 2/1 in favor of α-anomer. While treatment of 54 with silylated $N^4$-benzoylcytosine in the presence of $SnCl_4$, a complex 54-ii was formed instead of oxonium 54-i. Silyated $N^4$-benzoylcytosine attacked 54-ii from less stereohindered up-side to give a mixture of α/β-anomers with a ratio of 1/5 in favor of β-anomer.

Compound 54 can be made from the protected lactone of the formula, 49B, which can be reduced with DIBAL-H or lithium tri-tert-butoxyaluminum hydride and other hydride reducing agent to the lactol, which can then converted either to the acylate by acylation with acyl halide, or acyl anhydride, in presence of an appropriate base in an appropriate solvent. Acyl halide or acyl anhydride includes, but is not limited to the following list: acetic chloride, optionally substituted benzoyl chloride, acetic anhydride, optionally substituted benzoyl anhydride. The base includes, but is not limited to the following: imidazole, pyridine, 4-(dimethylamino)pyridine, triethyllamine, diisopropylethylamine, 1,4-diazabicyclo[2,2,2]octane. The solvent includes, but is not limited to the following list: pyridine, dichloromethane, chloroform, 1,2-dichloroethane, tetrahydrofuran.

(iii) Synthesis of the L-Nucleosides, IB-L

The processes for the D-series of the formula I and II can be used for preparation of the L-nucleosides of the formula, IB-L from the (S)-glyceraldehydes (Scheme 11).

Scheme 11

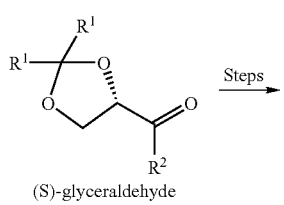

(S)-glyceraldehyde

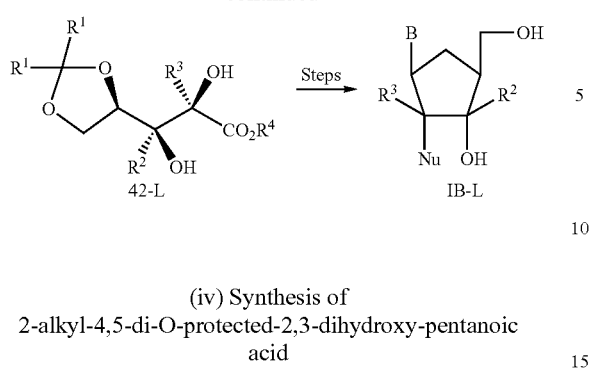

(iv) Synthesis of 2-alkyl-4,5-di-O-protected-2,3-dihydroxy-pentanoic acid

Currently, the most preferable procedure for the synthesis of nucleosides of general structures I and II is the preparation of a derivative of the 2-deoxy-2-fluoro-2-C-methyl-D-ribo-furanosyl moiety of I and II as shown in Scheme 4, Scheme 5 and Scheme 6, above through (i) synthesis of the intermediate, derivatives of 2-alkyl-4,5-di-O-protected-2,3-dihydroxy-pentanoic-acid ester of general structure I, (ii) conversion of 42B into the 3,5-protected 2-deoxy-2-fluoro-2-C-methyl-D-ribono-γ-lactone of general structure 49B, and (iii) conversion of 49B into purine and pyrimidine nucleosides of general structures of I and II. The key step in Scheme 4 is the stereoselective osmium catalyzed dihydroxylation of olefinic intermediate 41 into 42 in the presence of the expensive Sharpless AD catalyst. Instead of the Sharpless catalyst, if other chiral compounds such as L-quinidine are used, the reaction also goes smoothly giving the desired 42. Kishi et al. have proposed that in $OsO_4$ dihydroxylation of allylic alcohol derivatives (esters, ethers, acetals or ketals), the major course of reaction would occur on the face of the olefinic bond opposite to that of the preexisting hydroxyl or alkoxyl group, (Tetrahedron Lett, 1983, 24, 3943). Some examples are shown in Scheme 12 (Tetrahedron Lett, 1983, 24, 3947). In every case, the major product arose from addition of $OSO_4$ from the anti side of the oxygen on the neighboring secondary carbon. However, stereoselectivity is not high enough for preparative synthesis.

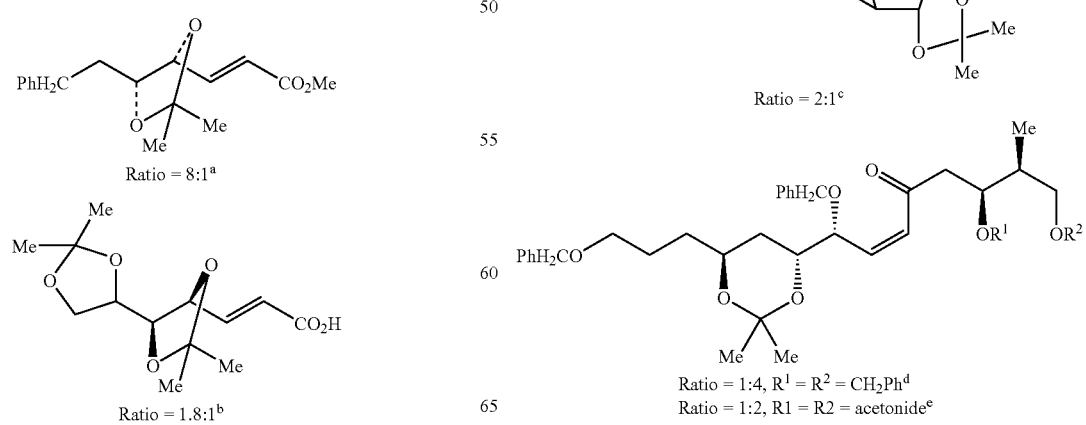

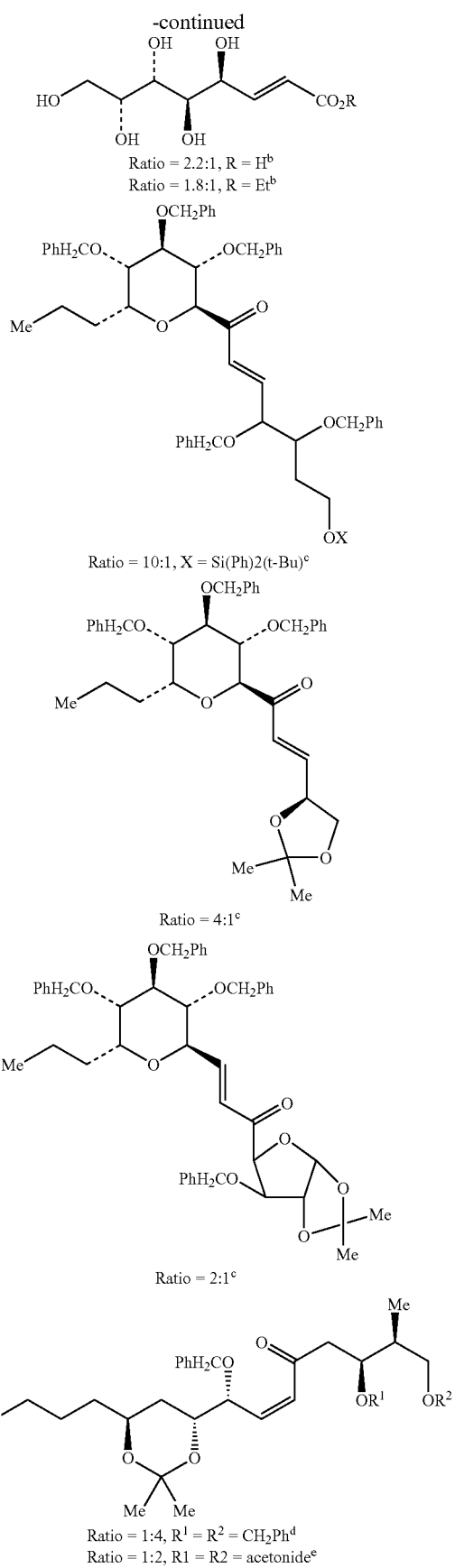

Encouraged by Kishi's rule, which presents that the stereochemistry is formulated as arising from the preferential approach of osmium tetroxide to occur on the face of the olefinic bond opposite to that of the preexisting hydroxyl or alkoxyl group, dihydroxylations of 41 under the original conditions but without any chiral catalysts, including Sharpless AD catalyst, were conducted. Dihydroxylation of 41 using $Ke_3Fe(CN)_6/K_2OsO_2(OH)_4/K_2CO_3$ system without chiral catalysts gives the product in 77% yield, which product is a 5:1 mixture of isomers with the predominant isomer being the desired 42. The reaction of olefin 41 with $OsO_4$ using N-methylmorpholine N-oxide (NMO) as the oxidant without chiral catalysts gave a 5:1 mixture of 42 and its isomer in 79% yield. Most surprisingly, when t-butylhydroperoxide (TBHP) is used as oxidant in the presence of catalytic amount of $OSO_4$ in acetone and ammonium acetate as buffer (the reagent combination was used in the synthesis of alditols by Masamune and Sharpless (J. Org. Chem, 1982, 47, 1373)), the crystalline product isolated is the virtually pure desired 42. This procedure is therefore far superior to the $OSO_4$/NMO and $Fe(CN)_6^{3-}$ methods. At 10 mmolar scale, the desired diol 42 is formed exclusively, and is isolated in 87% yield. No contamination by the other isomer was detected in this product by vigorous $^1H$ NMR analyses.

It is well known that in $OSO_4$ oxidation the intermediate is cyclic osmate V (below) (Criegee, *Liebigs Ann. Chem.*, 1936, 522, 75). cis-Dihydroxylation of olefins with potassium permanganate in alkaline media has been known for quite some time (Robinson and Robinson, *J. Chem. Soc.*, 1925, 127, 1628), and this reaction appears to proceed through a cyclic ester VI. Thus attempts at permanganate dihydroxylation have been performed.

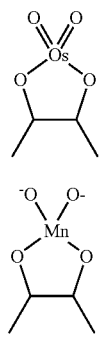

Previous reports have indicated that permanganate dihydroxylation of olefins in acid or neutral conditions causes over-oxidation of the initial diol products with concomitant production of ketones and carboxylates. Only in alkaline conditions further oxidation of the diol products can be decelerated. As 41 is a carboxylic ester the reaction cannot be done in aqueous alkali. Hazra et al. (J. Chem. Soc. Perkin Trans. I, 1994, 1667) describes successful dihydroxylation of highly substituted olefins to the corresponding diols using tetradecyltrimethylammonium permanganate (TDTAP) in a mixture of t-BuOH, dichloromethane and water in the presence of 0.1 equivalent of KOH. Application of this method to dihydroxylation of 41 results in rapid formation (within 10 minutes at room temperature) of a mixture of 42 and its diastereomer in an 8:1 ratio, which is isolated in 71% yield. Oxidation occurs much faster in similar reactions without KOH, but the yield of 42 is not improved.

Mukaiyama et al. (Chem. Lett., 1983, 173) disclosed dihydroxylation of olefins with $KMnO_4$ and 18-crown-6 ether in dichloromethane at $-40°$ C. Attempts at dihydroxylation of 41 under Mukaiyama's conditions but at different temperatures offer a 6:1 mixture of 42 and its diastereomer in 50% yield at $-40°$ C. and the same mixture in 94% yield at $-10°$ C.

Surprisingly, in contrast to the teaching of the prior of art which discloses that oxidation of a double bond with $KMnO_4$ proceeds via diol wherein the resultant diol is rapidly oxidized further without the presence of base, diol 42 was found to be isolable when the corresponding 41 is treated with $KMnO_4$ without added alkali and crown ether. In pure t-butanol, oxidation does not proceed even at room temperature conditions for two days. Addition of water to the mixture promotes the reaction. It is found that the more water in the reaction media the faster the reaction proceeds with poor selectivity of 42 production; the less water the slower the reaction but improved selectivity. In any case, the yield is rather poor due to further oxidation.

Most surprisingly, and in contradiction to the prior art, treatment of 41 with $KMnO_4$ in acetone is found to give a 10:1 mixture in quantitative yield, the desired 42 being the major component. The stereoselectivity is found to be improved by performing the reaction in a mixture of acetone and pyridine.

The following Examples are set forth to aid in an understanding of the invention. This section is not intended to, and should not be interpreted to, limit in any way the invention set forth in the claims which follow thereafter.

EXAMPLES

Example 1

(2S,3R,4R)-4,5-O-isopropylidene-2,3-O-sulfuryl-2,3,4,5-tetrahydroxy-2-methyl-pentanoic acid ethyl ester (IIIb, $R^1$=$CH_3$, $R^2$=H, $R^3$=$CH_3$)

To a solution of (2S,3R,4R)-4,5-O-isopropylidene-2,3,4,5-tetrahydroxy-2-methyl-pentanoic acid ethyl ester ($R^1$=$CH_3$, $R^2$=H, $R^3$=$CH_3$) (2.0 g, 8.06 mmol) in anhydrous methylene chloride (40 mL) containing triethyl amine (3.4 mL) was added at $0°$ C. thionyl chloride (0.88 mL, 12.08 mmol) dropwise over 10 min. The resulting reaction mixture was stirred at $0°$ C. for 10 min, diluted with cold ether (100 mL), washed with water (50 mL×2) and brine (50 mL×2), dried with sodium sulfate, and concentrated to give a residue (IIIa, $R^1$=$CH_3$, $R^2$=H, $R^3$=$CH_3$) which was dissolved in acetonitrile-tetrachloromethane (10:10 mL). To the obtained solution was added at room temperature sodium periodate (2.58 g, 12.06 mmol), ruthenium trichloride (16 mg, 0.077 mmol), and water (14 mL) subsequently. The resulting reaction mixture was stirred at room temperature for 10 min, diluted ether (100 mL), washed with water (50 mL×2), saturated sodium bicarbonate solution (50 mL×2), and brine (50 mL×2), dried with sodium sulfate, concentrated, and co-evaporated with toluene (30 mL×3) to a syrupy residue, the sulfate IIIb (2.23 g, 89%) which was used for the next reaction without further purification. $^1H$ NMR ($CDCl_3$) δ (ppm) 5.04 (d, 1H, J=9.6 Hz, H-3), 4.37 (m, 1H, H-4), 4.29 (q, 2H, J=7.6 Hz, $CH_2CH_3$), 4.17 (dd, 1H, J=5.6, 9.6 Hz, H-5), 4.05 (dd, 1H, J=3.2, 9.6 Hz, H-5'), 1.8 (s, 3H, $CH_3$-2), 1.38 (s, 3H, $(CH_3)_2C$), 1.32 (t, 3H, J=6.8 Hz, $CH_2CH_3$), 1.31 (s, 3H, $(CH_3)_2C$).

Example 2

Tetrabutylammonium salt of (2R,3S,4R)-2-fluoro-4, 5-O-isopropylidene-2-methyl-3-sulfooxy-3,4,5-trihydroxypentanoic acid ethyl ester (51B, $R^1$=$CH_3$, $R^2$=H, $R^3$=$CH_3$, Nu=F, $M^+$=tetrabutylammonium)

Method 1: To a solution of the sulfate IIIb from Example 1 (628 mg, 2.02 mmol) in anhydrous tetrahydrofuran was added at 0° C. tetrabutylammonium fluoride (1M in tetrahydrofuran, dried with 4 Å molecular sieves) dropwise over 5 min. The resulting reaction mixture was stirred at 0° C. for 20 min, another 2 m L of tetrabutylammonium fluoride (1M tetrahydrofuran, dried with 4 Å molecular sieves, 3 mL) was added, and then the reaction mixture was stirred at 0° C. for 2 hours, then concentrated, and purified by silica gel column chromatography (EtOAc) to give to the fluorinated sulfate, as a syrup (350 mg, 38%). $^1$H NMR ($CDCl_3$) δ (ppm) 4.66 (dd, 1H, J=9.6, 25.6 Hz, H-3), 4.48 (dd, 1H, J=5.2, 8.8 Hz, H-4), 4.20, 4.07 (2 m, 4H, H-5, $OCH_2CH_3$), 3.21 (m, 8H, N(C$\underline{H}_2CH_2CH_2CH_3)_4$), 1.69 (d, 3H, J=22.4 Hz, $CH_3$-2), 1.59 (m, 8H, N($CH_2\underline{CH}_2CH_2CH_3)_4$), 1.39 (m, 8H, $CH_2CH_2C\underline{H}_2CH_3)_4$), 1.27-1.25 (m, 9H, $OCH_2CH_3$, $(CH_3)_2C$), 0.96 (t, 12H, J=6.8 Hz, $CH_2CH_2CH_2C\underline{H}_3)_4$.

Method 2: To a solution of the cyclic sulfate IIIb (480 mg, 1.55 mmol) in anhydrous tetrahydrofuran was added at 0° C. tetrabutylammonium fluoride (1M in tetrahydrofuran, neutralized with HF-pyridine, 3.1 mL) dropwise over 5 min. The resulting reaction mixture was stirred for 39 hours, concentrated, and purified by silica gel column chromatography ($CH_2Cl_2$:MeOH=10:1) to the fluorinated sulfate as a syrup (280 mg, 39%).

Example 3

2-Deoxy-2-fluoro-2-C-methyl-D-ribono-γ-lactone (53B, $R^2$=H, $R^3$=$CH_3$, Nu=F)

A mixture of the product of Example 2 (170 mg, 0.370 mmol), trifluoroacetic acid (0.8 mL), and water (2 mL) in acetonitrile (10 mL) was heated at 80° C. for 1.5 hours, diluted with ethyl acetate (15 mL), washed with water (10 mL) and saturated sodium bicarbonate solution (10 mL). The aqueous layer was saturated with NaCl and extracted with ethyl acetate (10 mL). The combined organic layer was dried with sodium sulfate, filtered, and concentrated to give a residue, which was purified by silica gel column chromatography (hexanes:ethyl acetate=1:1 to $CH_2Cl_2$:MeOH=20:1) to give the desired compound as a white solid (60 mg, 100%). $^1$H NMR ($CDCl_3$) δ (ppm) 6.06 (d, 1H, J=6.8 Hz, H0-3), 5.16 (t, 1H, J=4.8 Hz, HO-5), 4.26 (m, 1H, H-4), 3.98 (ddd, 1H, J=7.2, 8.0, 23.2 Hz, H-3), 3.78 (ddd, 1H, J=2.0, 5.2, 12.8 Hz, H-5), 3.55 (ddd, 1H, J=4.4, 5.6, 12.4 Hz, H-5'), 1.48 (d, 3H, J=24 Hz, $CH_3$-2); $^{13}$C NMR ($CDCl_3$) (ppm) 171.2 (d, J=21.2 Hz, C-1), 92.5 (d, J=177.5 Hz, C-2), 83.37 (C-4), 70.2 (d, J=15.9 Hz, C-3), 59.0 (C-5), 17.1 (d, J=25.0 Hz, $\underline{CH}_3$—C-2).

Example 4

3,5-Di-O-benzoyl-2-deoxy-2-fluoro-2-C-methyl-D-ribono-γ-lactone (49B, $R^2$=H, $R^3$=$CH_3$, $R^5$=Bz, $R^6$=Bz, Nu=F)

The compound of Example 3 (60 mg, 0.16 mmol) was dissolved in anhydrous pyridine (1 mL) and benzoyl chloride (0.3 mL) was added. The resulting reaction mixture was stirred at room temperature for 20 min, water added (1 mL), stirred for 20 min, diluted with ethyl acetate (5 mL), washed with water (2 mL) and 1M HCl (2 mL×3), and dried with sodium sulfate. Upon filtration and concentration, the residue was purified by silica gel column chromatography (hexanes: ethyl acetate=10:1) to give 3,5-di-O-benzoyl-2-deoxy-2-fluoro-D-ribono-γ-lactone as a white solid (118 mg, 87%). $^1$H NMR ($CDCl_3$) δ (ppm) 8.08 (m, 2H, aromatic), 7.99 (m, 2H, aromatic), 7.63 (m, 1H, aromatic), 7.58 (m, 1H, aromatic), 7.49 (m, 2H, aromatic), 7.43 (m, 2H, aromatic), 5.51 (dd, 1H, J=7.2, 17.6 Hz, H-3), 5.00 (m, 1H, H-4), 4.78 (dd, 1H, J=3.6, 12.8 Hz, H-5), 4.59 (dd, 1H, J=5.2, 12.8 Hz, H-5'), 1.75 (d, 3H, J=23.6 Hz, $CH_3$-2)

Example 5

Tetraethylammonium salt of (2R,3S,4R)-4,5-dihydroxy-2-fluoro-4,5-O-isopropylidene-2-methyl-3-sulfooxy-pentanoic acid ethyl ester (51B, $R^1$=$CH_3$, $R^2$=H, $R^3$=$CH_3$, Nu=F, tetraethylammonium)

Method 1. To a solution of the sulfate IIIb (Scheme 9) (1.96 g, 6.32 mmol) in anhydrous N,N-dimethylformamide (20 mL) was added at 0° C. tetraethylammonium fluoride hydrate (1.39 g, 9.13 mmol) in one portion. The resulting reaction mixture was stirred for 30 min, concentrated, and co-evaporated with toluene to give a semi-solid (51b) (3.35 g, crude, proton NMR showed virtually one product). $^1$H NMR ($CDCl_3$) δ (ppm) 4.61 (dd, 1H, J=9.2, 25.6 Hz, H-3), 4.51 (dd, 1H, J=5.2, 9.2 Hz, H-4), 4.23-4.05 (m, 4H, H-5, $OCH_2CH_3$), 3.32 (q, 8H, J=7.2 Hz, N($CH_2CH_3)_4$), 1.69 (d, 3H, J=23.2 Hz, $CH_3$-2), 1.31-1.24 (m, 21H, $OCH_2C\underline{H}_3$, $(C\underline{H}_3)_2C$, N($CH_2C\underline{H}_3)_4$.

Method 2: To a solution of the sulfate IIIb (148 mg, 0.477 mmol) in anhydrous acetonitrile (2 mL) was added at 0° C. tetraethylammonium fluoride hydrate (107 mg, 0.717 mmol) in one portion. The resulting reaction mixture was stirred for 24 hours, concentrated, and co-evaporated with toluene to give a semi-solid (257 mg, crude, proton NMR showed virtually one product).

Example 6

Preparation of 1-(2-deoxy-2-fluoro-2-methyl-3,5-O-3,5 dipivaloyl-ribofuranosyl)-$N^4$-benzoylcytosine (11b, $R^5$=$R^6$=pivaloyl, $R^2$=H, $R^3$=Me)

To a solution of 49B, (Scheme 6) (Nu=F, $R^2$=H, $R^3$=Me, $R^5$=$R^6$=pivaloyl, 3.44 g, 10.36 mmol) in THF (70 mL) was added LiAl(t-BuO)$_3$H (13.47 mmol, 1M in THF, 13.47 mL) at −20° C. to −10° C. and the resulting solution was stirred at −10° C. to −15° C. for 2 h. To the solution was added an additional LiAl (t-BuO)$_3$H (1.35 mL, 1.35 mmol) and the solution was stirred at −10° C. for 1 h. Ice water (50 mL) was added. The mixture was extracted with EtOAc (200 mL), and the organic layer was washed with water, brine and dried ($Na_2SO_4$). Solvent was removed to give crude lactol which was dissolved in $CH_2Cl_2$ (50 mL). To the solution were added $Et_3N$ (31.08 mmol, 4.24 mL), 4-dimethylaminopyridine (1 mmol, 122 mg) and trimethylacetyl chloride (20.7 mmol, 2.55 mL), and the mixture was stirred at room temperature for 16 h. Water (20 mL) was added, and the resulting mixture was stirred at room temperature for 10 min. EtOAc (200 mL) was added, and organic solution was washed with water, brine, and dried ($Na_2SO_4$). Solvent was removed and the residue was co-evaporated with toluene (2×20 mL) to give a crude intermediate (5, 6.74 g) for the next coupling reaction without purification.

A suspension of N⁴-benzoylcytosine (6.06 mmol, 1.30 g) and $(NH_4)_2SO_4$ (30 mmg) in HMDS (16.7 mL) was refluxed for 5 h, and the clear solution was concentrated to dryness under reduced pressure. The residue was dissolved in 1,2-dichloroethane (50 mL). To the solution were added crude 54 (1.96 g, Scheme 6) and $SnCl_4$ (1.42 mL, 12.12 mmol) at room temperature. The solution was refluxed for 24 h. and cooled to 0° C. To the solution were added $NaHCO_3$ (6.11 g, 72.72 mmol) and EtOAc (50 mL). To the mixture was added $H_2O$ (2 mL) slowly, and the resulting mixture was stirred at room temperature for 20 min. Solid was removed by filtration. The organic solution was washed with water, brine and dried ($Na_2SO_4$). Solvent was removed to give syrup as crude mixture of β/α-anomers with a ratio of 4/1 in favor to β-isomer. The crude product was dissolved in MeOH (1 mL) at 50° C. To the solution was added hexanes (10 mL). The mixture was allowed to stay at room temperature for 1 h, then 0° C. for 2 h. Crystals were collected by filtration, washed with hexanes to give product 55, Scheme 6 (323 mg, 20.3% from 49). Mother liquor was concentrated to dryness and purified by column chromatography (20-50% EtOAc in hexanes) to give second crop of 55. H-NMR ($CDCl_3$): δ 8.82 (br s, 1H, NH), 8.10, 7.89, 7.62, 7.52 (m, 7H, H-5, H-6, 5 Ph-H), 6.41 (d, J=18.4 Hz, 1H, H-1'), 5.10 (m, 1H, H-3'), 4.45 (d, J=9.6 Hz, 1H, H-4'), 4.36 (t, J=2.8 Hz, 2H, H-5'), 1.35 (d, J=22.0 Hz, 3H, Me), 1.29, 1.23 [ss, 18H, $C(Me)_3$].

Example 7

(2S,3R)-3-[(4R)-2,2-Dimethyl-[1,3]dioxolan-4-yl]-2, 3-dihydroxy-2-methyl-propionic acid ethyl ester (42)

4-Methylmorpholine N-Oxide as Oxidant with Osmium Catalyst

To a stirred solution of compound 41 (214 mg, 0.1 mmol) in t-BuOH under argon was added a solution of 4-methylmorpholine N-oxide (0.47 mL, 50 wt % solution in $H_2O$) and water (0.2 mL). A 2.5 wt % solution of osmium tetraoxide in tert-butyl alcohol (0.51 mL) is added, and the mixture is stirred for 5 h at room temperature in a water bath. The mixture is evaporated in vacuo to a syrup, which is azeotroped with $H_2O$ (3×10 mL) to remove 4-methylmorpholine. The residue is dried by addition and evaporation of EtOH (2×10 mL) to give a residue, which was purified by silica gel column chromatography with 20% EtOAc in hexanes to provide the desired product and its isomer (196 mg, 79%) as a solid. Proton NMR indicates that the ratio of the desired product to its isomer is around 5:1. Recrystallization of the mixture from hexanes/ethyl acetate gives pure product (91 mg, 37.4% from starting material) as a crystalline solid. $^1H$ NMR (DMSO-$d_6$) δ 1.18 (t, J=7.2 Hz, 3H, —$OCH_2CH_3$), 1.24 (s, 3H, $CH_3$), 1.25 (s, 3H, $CH_3$), 1.28 (s, 3H, 2-$CH_3$), 3.67 (t, J=7.2 Hz, 1H), 3.85, 4.06 and 4.12 (m, 4H), 4.97 (s, 1H, 2-OH, $D_2O$ exchangeable), 5.14 (d, J=7.6 Hz, 2-OH, $D_2O$ exchangeable).

Example 8

(2S,3R)-3-[(4R)-2,2-Dimethyl-[1,3]dioxolan-4-yl]-2, 3-dihydroxy-2-methyl-propionic acid ethyl ester (42)

Potassium Ferricyanide as Oxidant with Osmium Catalyst

A 100 mL round-bottomed flask, equipped with a magnetic stirrer, is charged with 5 mL of tert-butyl alcohol, 5 mL of water, and a mixture of $K_3Fe(CN)_6$ (0.98 g), $K_2CO_3$ (0.41 g), and $K_2OsO_2(OH)_4$ (3.2 mg). Stirring at room temperature produced two clear phases; the lower aqueous phase appears bright yellow. Methanesulfonamide (95 mg) is added at this point. The mixture is cooled to 0° C. whereupon some of salts precipitate out, 214 mg (1 mmol) of the compound 41 is added at once, and the heterogeneous slurry is stirred vigorously at 0° C. for 24 h. To the mixture is added solid sodium sulfite (1.5 g) while stirring at 0° C., and then the mixture is allowed to warm to room temperature and stirred for 30-60 min. Ethyl acetate (10 mL) is added, and after separation of the layers, the aqueous phase is further extracted with EtOAc. The organic layer is dried over $Na_2SO_4$ and concentrated to dryness. The residue is purified by silica gel column chromatography with 20% EtOAc in hexanes to provide the product (190 mg, 77%) as a solid, proton NMR indicates that the ratio of the desired product to its isomer is around 5:1. Recrystallization of the mixture with hexanes/ethyl acetate gave pure diol product (102 mg, 41% from starting material) as a crystalline solid. The $^1H$ NMR spectrum of this product is identical to that of an authentic specimen.

Example 9

(2S,3R)-3-[(4R)-2,2-Dimethyl-[1,3]dioxolan-4-yl]-2, 3-dihydroxy-2-methyl-propionic acid ethyl ester (42)

t-Butylhydroperoxide as Oxidant at Room Temperature with Osmium Catalyst

A 50 mL of flask, equipped with magnetic stirrer, is charged with 2 mL of acetone, 214 mg (1 mmol) of compound 41, 65 mg of $Et_4NOAc.4H_2O$, and 0.3 mL of tert-butyl hydroperoxide (5~6 M in decane). After stirring at room temperature until the $Et_4NOAc$ a clear solution is obtained, the resulting solution is cooled in an ice bath and 5 mL of $OsO_4$ (2.5 wt % in t-BuOH) is added in one portion. The solution immediately becomes brownish purple. After 1 h the ice bath is removed and the reaction mixture is allowed to warm to room temperature and stirred for 14 h. The rest of the procedure is done exactly the same way as described above. After flash column chromatography, 178 mg (72%) of product is obtained as a solid. In an expanded $^1H$ NMR, a tiny bump is observed at δ 1.26 indicating the presence of an isomer in less than 4% in the product Example 10

(2S,3R)-3-[(4R)-2,2-Dimethyl-[1,3]dioxolan-4-yl]-2, 3-dihydroxy-2-methyl-propionic acid ethyl ester (42)

t-Butyhydroperoxide as Oxidant at 0° C. with Osmium Catalyst

A 250 mL of flask, equipped with magnetic stirrer, is charged with 20 mL of acetone, 2.14 g (10 mmol) of compound 41, 650 mg of $Et_4NOAc._4H_2O$, and 3 mL of tert-butyl hydroperoxide (5~6 M in decane). After stirring at room temperature until the $Et_4NOAc$ has dissolved, the resulting solution is cooled in an ice bath and 5 mL of $OsO_4$ (2.5 wt % in t-BuOH) is added in one portion. The solution immediately becomes brownish purple. The reaction mixture is then stirred at 0° C. for 6.5 h (monitored by TLC, hexanes:ethyl acetate=4:1, Rf=0.18). Ether (40 mL) is added at 0° C. and the resulting mixture is treated with 5 mL of freshly prepared 10% $NaHSO_3$ solution in one portion. The ice bath is removed and stirring is continued for 1 h. EtOAc (100 mL) and $H_2O$ (50 mL) are added to the mixture. After separation of the

Example 11

(2S,3R)-3-[(4R)-2,2-Dimethyl-[1,3]-dioxolan-4-yl]-
2,3-dihydroxy-2-methyl-propionic acid ethyl ester
(42)

Tetradecyltrimethylammonium Permanganate
(TDTAP) as Oxidant

To a stirred solution of compound 41 (214 mg, 1 mmol), in t-BuOH (10 mL) and $CH_2Cl_2$ (2 mL) at room temperature is added a solution of KOH (6 mg, 0.1 mmol) in water followed by TDTAP (0.420 g, 1.12 mmol) in small portions over a period of five minutes. TLC after 5 minutes showed that the reaction is complete. The solution is quenched by using 10 mL of saturated sodium bisulfite. The reaction mixture is concentrated in vacuo and the residue extracted with ethyl acetate (3×15 mL), dried ($Na_2SO_4$), evaporated to give a white solid, which is further dissolved in 5 mL of $CH_2Cl_2$, passed it through a plug of silica gel topped with Celite, washed with ethyl acetate (50 ml). The filtrate is dried in vacuo to give viscous oil (174 mg 71% yield) as an 8:1 mixture of which the predominant isomer is the titled compound.

Example 12

(2S,3R)-3-[(4R)-2,2-Dimethyl-[1,3]dioxolan-4-yl]-2,
3-dihydroxy-2-methyl-propionic acid ethyl ester (42)

Potassium Permanganate as Oxidant with
18-Crown-6 Ether-A (at −40° C.)

To a solution of compound 41 (214 mg, 1 mmol) in $CH_2Cl_2$ (10 mL) and 18-crown-6-ether (37.5 mg, 0.1 mmol) is added $KMnO_4$ (158 mg, 1 mmol) in portions at −40° C., and the mixture stirred for 2 h at the same temperature. During this time the reaction mixture turns to dark brown. After the reaction was complete, mixture is quenched with saturated solution of sodium bisulfite (10 mL). The resulting colorless mixture is filtered through a frit, and extracted the filtrate with ethyl acetate (2×25 ml), dried ($Na_2SO_4$) and concentrated to give a viscous oil consisting of 10-20% of unreacted olefin starting material along with the desired diols and its isomer in a ratio of 6:1 ($^1$H NMR). Olefin starting material can be removed by passing through a small pad of silica gel using 5% ethyl acetate:hexane. A 6:1 mixture of the desired diols is eluted from the column with 20% ethyl acetate/hexane, and obtained as a white solid (200 mg ~80%) upon evaporation of the solvent.

Example 13

(2S,3R)-3-[(4R)-2,2-Dimethyl-[1,3]-dioxolan-4-yl]-
2,3-dihydroxy-2-methyl-propionic acid ethyl ester
(42)

Potassium Permanganate as Oxidant with
18-Crown-6 Ether-B (at −10° C.)

To a solution of compound 41 (214 mg, 1 mmol) in $CH_2Cl_2$ (10 ml) is added 37.5 mg (0.1 mmol) of 18-crown-6-ether, and mixture is cooled to −10° C. $KMnO_4$ (237 mg, 1.5 mmol) is added in portions, and the mixture stirred at −10° C. for 2 h. During this time the reaction mixture turns to dark brown, which is treated with saturated solution of sodium bisulfite (10 mL). The resulting mixture is filtered through a frit, and the filtrate is extracted with ethyl acetate (2×25 ml), dried ($Na_2SO_4$) and evaporated to give a white solid (240 mg, 94.4%) consisting of the desired product and its isomer in a ratio of 6:1.

Example 14

(2S,3R)-3-[(4R)-2,2-Dimethyl-[1,3]dioxolan-4-yl]-2,
3-dihydroxy-2-methyl-propionic acid ethyl ester (42)

Potassium Permanganate as Oxidant in 1:9
$H_2O$/t-BuOH

To a solution of compound 41 (214 mg, 1 mmol) in t-BuOH (9 mL) and $H_2O$ (1 mL) at 0° C. is added $KMnO_4$ (237 mg, 1.5 mmol) in portions and the mixture stirred at the same temperature for 2 h. An additional amount (79 mg, 0.5 mmol) of $KMnO_4$ is charged and the mixture is stirred for another 30 minutes. After work up as above, 128 mg (50%) of a mixture of isomers in a ratio of 8:1 is obtained as a white solid in which the major component is the desired product.

Example 15

(2S,3R)-3-[(4R)-2,2-Dimethyl-[1,3]-dioxolan-4-yl]-
2,3-dihydroxy-2-methyl-propionic acid ethyl ester
(42)

Potassium Permanganate as Oxidant in 9:1
$H_2O$/t-BuOH

To a solution of compound 41 (214 mg, 1 mmol) in $H_2O$ (9 mL) and t-BuOH (1 mL) at 0° C. is added $KMnO_4$ (237 mg, 1.5 mmol) in portions and stirred at the same temperature for 30 minutes. During this time the mixture turns to dark brown. Saturated solution of sodium bisulfite (10 mL) is added to the mixture, which is filtered, and the filtrate is extracted with ethyl acetate (3×25 ml), dried ($Na_2SO_4$), and concentrated to give a 4:1 mixture of diol isomers as a white solid (128 mg, 50%), in which the titled compound is the major component.

Example 16

(2S,3R)-3-[(4R)-2,2-Dimethyl-[1,3]dioxolan-4-yl]-2,
3-dihydroxy-2-methyl-propionic acid ethyl ester (42)

Potassium Permanganate as Oxidant in H2O at 0° C.

A solution of $KMnO_4$ (158 mg, 1.0 mmol) in $H_2O$ (10 mL) is added to compound 41 (214 mg, 1 mmol), and the mixture is stirred at 0° C. for 1 hour. The reaction mixture is quenched with saturated solution of sodium bisulfite (10 mL), and the mixture is worked up as above. A white solid (80 mg, 32%) that is obtained is a 4:1 mixture of diol isomers in which the titled compound is the predominant component.

Example 17

(2S,3R)-3-[(4R)-2,2-Dimethyl-[1,3]dioxolan-4-yl]-2,
3-dihydroxy-2-methyl-propionic acid ethyl ester (42)

Potassium Permanganate as Oxidant in Acetone

To a solution of compound 41 (214 mg, 1 mmol) in acetone (10 mL) is added 37.5 mg, 0.1 mmol) and cooled the reaction mixture to 0° C. To this cold solution is added KMnO₄ (237 mg, 1.5 mmol) in portions, and the reaction mixture is stirred for 2 h at the same temperature. During this time the reaction mixture turns to dark brown. The reaction mixture is quenched with saturated solution of sodium bisulfite (10 ml) where the solution becomes colorless. The reaction mixture is extracted with ethyl acetate (3×25 ml), dried and evaporated the mixture to give a white solid (245 mg, 96.4%) in the ratio of 10:1.

Example 18

(2S,3R)-3-[(4R)-2,2-Dimethyl-[1,3]dioxolan-4-yl]-2, 3-dihydroxy-2-methyl-propionic acid ethyl ester (42)

Potassium Permanganate as Oxidant in a Mixture of Acetone and Pyridine

To a solution of compound 41 (214 mg, 1 mmol) in a mixture of acetone (9 mL) and pyridine (1 mL) at 0° C. is added KMnO₄ (158 mg, 1.0 mmol) and stirred at same temperature for 1 hr. After work up of the reaction mixture as above, 164 mg (67%) of white solid which is practically pure product. Vigorous ¹H NMR analyses reveal the crude white solid contains about 6% of the diastereomer of the titled compound.

Example 19

(2S,3R)-3-[(4R)-2,2-Dimethyl-[1,3]dioxolan-4-yl]-2, 3-dihydroxy-2-methyl-propionic acid ethyl ester (42) in the RuCl₃/CeCl₃/NaIO₄ system In a 50 mL round-bottomed flask equipped with magnetic stirring bar, a mixture of NaIO₄ (321 mg, 1.5 mmol) and CeCl₃·7H₂O (37 mg, 0.1 mmol) in 0.45 mL of water is stirred and gently heated until a bright yellow suspension is formed. After cooling to 0° C., EtOAc (1.25 mL) and acetonitrile (1.5 mL) are added and the suspension is stirred for 2 minutes. A 0.1 M aqueous solution of RuCl₃ (25 μL) is added and the mixture is stirred for 2 minutes. A solution of the compound 41, (214 mg, 1 mmol) in EtOAc (0.25 mL) is added in one portion and the resulting slurry is stirred at 0° C. for 1 hour. Solid Na₂SO₄ (0.5 g) is added followed by EtOAc (3 mL). The solid is filtered off, and the filter cake is washed several times with EtOAc. Then the filtrate is washed with saturated Na₂SO₃ solution and the organic layer is dried (Na₂SO₄) and concentrated to dryness. The residue is purified by silica gel column chromatography with 20% EtOAc in hexanes to provide a syrup (150 mg, 60%). ¹H NMR indicates that the ratio of the desired product to its isomer is approximately 1.6:1.

Example 20

Reduction and Acylation of Compound 49

To a solution of 3,5-dibenzoyl-2-fluoro-2-deoxy-2-methyl-D-ribono-lactone (49, 23 g, 61.77 mmol, scheme 6) in anhydrous THF (400 ml) was added LiAl ('-OBu)₃H (75 mL 1M in THF, 75.0 mmol) over a period of 15 min at −20 to −10° C. and the resulting solution was stirred at the same temperature until all the starting material was consumed. After 5 hours, ~10-20% starting material was left, therefore additional 10 mL of LiAl(t-OBu₃H (10 mmol) was added at the same temperature and stirred for an hour when TLC indicated all starting material was consumed. To this reaction mixture were added DMAP (7.5 g) and Ac₂O (58.2 g, 616 mmol) and the solution was stirred at −10° C. for ~2-3 h. Upon completion of reaction (as indicated by TLC) the reaction mixture was diluted with ethyl acetate (400 ml) and 200 ml of water. The organic layer was separated and the aqueous layer was washed with ethyl acetate (2×100 ml). The combined organic layer was washed with water (3×150 ml), brine and dried over anhy. Na₂SO₄. The solvent was removed under reduced pressure and coevaporated with toluene (2×100 mL) to give crude acetate as a clear brown oil. This oil was passed through a plug of silica gel (50 g) and washed with 20% ethyl acetate/hexanes until all the acetate was recovered. The solvent was evaporated under reduced pressure to give the desired acetate (54, 32 g) as a colorless oil.

Example 21

1-(2-deoxy-2-fluoro-2-methyl-3-5-O-dibenzoyl-β-D-ribofuranosyl)-N4-benzoylcytosine (55)

To a suspension of N⁴-benzoylcytosine (20.39 g, 94.74 mmol) in 400 ml of HMDS was added (NH₄)₂SO₄ (250 mg) and heated under reflux for 4 h. Excess HMDS was removed under reduced pressure. The oily residue was dissolved in chlorobenzene (1 L). To this solution were added a solution of the acetate (25 g) in chlorobenzene (250 mL) and SnCl₄ (190.4 mmol, 49 g) and the mixture was stirred at room temperature for 2 h followed by heating at ~65° C. for 16 h. The reaction mixture was cooled to 0° C. to which NaHCO₃ (96 g, 1.14 mol) and ethyl acetate (500 ml) were added followed by careful addition of water (20 ml). This mixture was allowed to stir at room temperature for 30 min. The mixture was filtered under vacuum, the residue washed with ethyl acetate. The organic layer was washed with water, brine (2×250 mL) and dried over anhydrous Na₂SO₄. Solvent was removed under reduced pressure to give a pale yellowish-brown solid. This was dissolved in MeOH (250 mL) heated under reflux for 30 minutes, cooled to room temperature and filtered, to give the desired product (55, 8.0 g) as a off-white solid.

Example 22

1-(2-deoxy-2-fluoro-2-C-methyl-β-D-ribofuranosyl) cytosine (14)

A suspension of 55 from Example 21 (16.7 g, 30.8 mmol, scheme 6) was treated with methanolic ammonia (750 mL, 7M in MeOH) and stirred at room temperature for 12 h and concentrated to dryness under reduced pressure to give pale yellow solid. THF (400 mL) was added to the solid and heated under reflux for 30 minutes and cooled to room temperature. The solid formed was collected by filtration and washed with THF to give 14 (6.7 g, 88%) as an off-white powder.

We claim:
1. A compound of the following general formula, 49B:

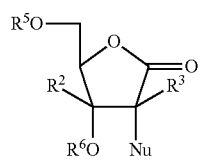

wherein
R² is independently hydrogen, a (C₁-C₆) alkyl, hydroxymethyl, methoxymethyl, halomethyl, vinyl, halovinyl, ethynyl, haloethynyl, allyl, or haloallyl;
R³ is independently a (C₁-C₆) alkyl, hydroxymethyl, methoxymethyl, halomethyl, vinyl, halovinyl, ethynyl, haloethynyl, allyl, or haloallyl;
R⁵, R⁶ are independently H, methyl, benzyl, trityl, triethylsilyl, t-butyldimethylsilyl, t-butyldiphenylsilyl, ethoxymethyl, methoxymethyl (MOM), methoxyethyl (MEM), benzyloxymethyl (BOM), acetyl, benzoyl, pivaloyl, 2-, 3-, or 4-nitrobenzoyl, 2-, 3-, or 4-chlorobenzoyl, or toluoyl; and
Nu is F, Cl, N₃, CN, NO₂, CF₃, SCN, OR or NR₂,
wherein R is independently selected from the group consisting of arylalkyl, a (C₁-C₆) alkyl, and CH₂R',
wherein R' is hydrogen or a (C₁-C₆) alkyl.

2. A process for the preparation of a compound of formula 49B:

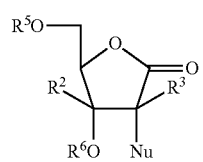

49B wherein
R² is independently hydrogen, a (C₁-C₆) alkyl, hydroxymethyl, methoxymethyl, halomethyl, vinyl, halovinyl, ethynyl, haloethynyl, allyl, or haloallyl;
R³ is independently a (C₁-C₆) alkyl, hydroxymethyl, methoxymethyl, halomethyl, vinyl, halovinyl, ethynyl, haloethynyl, allyl, or haloallyl;
R⁵, R⁶ are independently H, methyl, benzyl, trityl, triethylsilyl, t-butyldimethylsilyl, t-butyldiphenylsilyl, ethoxymethyl, methoxymethyl (MOM), methoxyethyl (MEM), benzyloxymethyl (BOM), acetyl, benzoyl, pivaloyl, 2-, 3-, or 4-nitrobenzoyl, 2-, 3-, or 4-chlorobenzoyl, or toluoyl; and
Nu is F, Cl, N₃, CN, NO₂ CF₃, SCN, OR or NR₂,
wherein R is independently selected from the group consisting of arylalkyl, a (C₁-C₆) alkyl, and CH₂R',
wherein R' is hydrogen or a (C₁-C₆) alkyl, the process comprising the steps of:
(a) treating a compound of formula 51B or 52B:

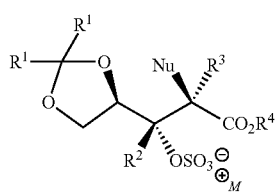

51B

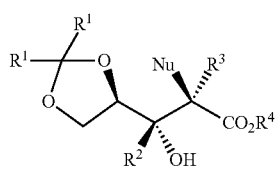

52B with an acid in at least one solvent,
wherein
R¹ is independently a (C₁-C₆) alkyl, phenyl, or benzyl; alternatively, R¹ is an ethylene (—CH₂CH₂—), or a trimethylene (—CH₂CH₂CH₂—) which forms a cyclopentyl or a cyclohexyl;
R⁴ is independently hydrogen, aryl, arylalkyl, or a (C₁-C₆) alkyl; and
M⁺ is tetrabutylammonium, tetraethylammonium, tetramethylammonium, sodium, potassium, cesium, rubidium, or silver;

(b) optionally, followed by azeotropic distillation in benzene or toluene in presence of acid to provide a compound of formula 53B; and

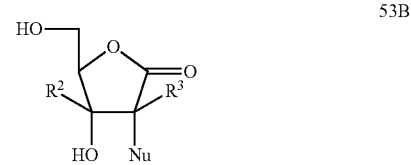

53B (c) protection of a compound of formula 53B with a protecting agent and a base in a solvent.

3. The process of claim 2, wherein the acid from either step (a) or step (b) is selected from one or more of the group consisting of HCl, H₂PO₃, H₂SO₄, TsOH, CH₃CO₂H, CF₃CO₂H and HCO₂H.

4. The process of claim 2, wherein the solvent from step (a) is selected from one or more of the group consisting of MeOH, EtOH, i-PrOH, CH₃CN, THF and water.

5. The process of claim 2, wherein compound 53B from step (c) is protected with:

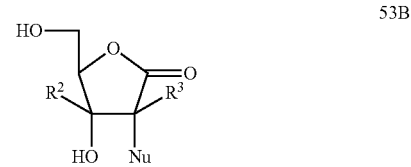

53B a protecting agent selected from one or more of the group consisting of methoxymethyl chloride, methoxyethyl chloride, benzyloxymethyl chloride, ethoxymethyl chloride, trityl chloride, triethylsilyl chloride, t-butyldimethylsilyl chloride, t-butyldiphenylsilyl chloride, acetyl chloride, acetic anhydride, benzoic anhydride, benzoyl chloride, toluoyl chloride, 4-phenylbenzoyl chloride, 2-, 3-, or 4-nitrobenzoyl chloride, and 2-, 3-, or 4-chlorobenzoyl chloride; and a base in a solvent.

6. The process of claim 5, wherein the base is selected from one or more of the group consisting of imidazole, pyridine, 4-(dimethylamino)pyridine, triethylamine, diisopropylethylamine, and 1,4-diazabicyclo[2,2,2]octane.

7. The process of claim 5, wherein the solvent is selected from one or more of the group consisting of pyridine, dichloromethane, chloroform, and 1,2-dichloroethane, and tetrahydrofuran.

* * * * *